US011239439B2

(12) United States Patent
Adachi et al.

(10) Patent No.: US 11,239,439 B2
(45) Date of Patent: Feb. 1, 2022

(54) MATERIAL FOR ORGANIC ELECTROLUMINESCENT DEVICE, LIGHT-EMITTING MATERIAL, AND ORGANIC ELECTROLUMINESCENT DEVICE

(71) Applicants: Hodogaya Chemical Co., Ltd., Tokyo (JP); Hirata Corporation, Kumamoto (JP); Kyushu University, National University Corporation, Fukuoka (JP)

(72) Inventors: Chihaya Adachi, Fukuoka (JP); Jun-Ichi Nishide, Kumamoto (JP); Yasuhide Hiraga, Kumamoto (JP); Takehiro Takahashi, Tokyo (JP)

(73) Assignees: Hodogaya Chemical Co., Ltd., Tokyo (JP); Hirata Corporation, Kumamoto (JP); Kyulux, Inc., Fukuoka (JP)

( * ) Notice: Subject to any disclaimer, the term of this patent is extended or adjusted under 35 U.S.C. 154(b) by 401 days.

(21) Appl. No.: 15/560,681

(22) PCT Filed: Mar. 14, 2016

(86) PCT No.: PCT/JP2016/057918
§ 371 (c)(1),
(2) Date: Sep. 22, 2017

(87) PCT Pub. No.: WO2016/152605
PCT Pub. Date: Sep. 29, 2016

(65) Prior Publication Data
US 2018/0108857 A1   Apr. 19, 2018

(30) Foreign Application Priority Data
Mar. 23, 2015 (JP) .............................. JP2015-059492

(51) Int. Cl.
*H01L 51/50* (2006.01)
*C07D 209/86* (2006.01)
*C09K 11/06* (2006.01)

(52) U.S. Cl.
CPC ........ *H01L 51/5056* (2013.01); *C07D 209/86* (2013.01); *C09K 11/06* (2013.01);
(Continued)

(58) Field of Classification Search
None
See application file for complete search history.

(56) References Cited

U.S. PATENT DOCUMENTS 6,562,982 B1 * 5/2003 Hu ....................... C07D 209/86
548/440
8,921,832 B2   12/2014 Lee et al.
(Continued)

FOREIGN PATENT DOCUMENTS

EP   2343277 A2   7/2011
EP   2471771 A1   7/2012
(Continued)

OTHER PUBLICATIONS

A.S.D. Sandanayaka et al., "Exciton Quenching Behavior of Thermally Activated Delayed Fluorescence Molecules by Charge Carriers," The Journal of Physical Chemistry, vol. 119, Mar. 24, 2015, pp. 7631-7636.
(Continued)

*Primary Examiner* — Gregory D Clark
(74) *Attorney, Agent, or Firm* — Locke Lord LLP; James E. Armstrong, IV; Nicholas J. DiCeglie, Jr.

(57) ABSTRACT

To provide a light-emitting material of a light emitting layer, particularly a dopant material or a host material of a light emitting layer emitting delayed fluorescence, or a material
(Continued)

suitable for a hole blocking layer, as a material for an organic electroluminescent device having a high efficiency, and also to provide an organic photoluminescent device or an organic electroluminescent device having a high efficiency and a high luminance, particularly an organic EL device suppressed in the roll-off phenomenon, by using the material. A material for an organic electroluminescent device, containing a benzonitrile derivative of the following general formula (1), and an organic electroluminescent device containing a pair of electrodes and one layer or plural layers including at least a light emitting layer intervening between the electrodes, the organic electroluminescent device using the material.

[Chemical Formula 1]

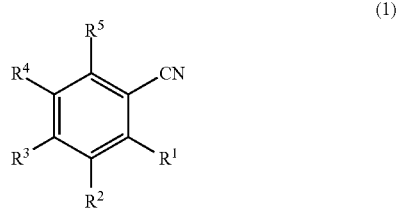

(1)

17 Claims, 4 Drawing Sheets

(52) U.S. Cl.
CPC .......... *H01L 51/50* (2013.01); *H01L 51/5072* (2013.01); *H01L 51/5092* (2013.01)

(56) References Cited

U.S. PATENT DOCUMENTS

| | | | |
|---|---|---|---|
| 9,502,668 | B2 | 11/2016 | Adachi et al. |
| 9,732,036 | B2 | 8/2017 | Yokoyama et al. |
| 2008/0174237 | A1 | 7/2008 | Kim et al. |
| 2009/0072727 | A1* | 3/2009 | Takeda .................. C09K 11/06 313/504 |
| 2010/0171418 | A1 | 7/2010 | Kinoshita et al. |
| 2010/0244676 | A1 | 9/2010 | Kinoshita |
| 2011/0193074 | A1 | 8/2011 | Lee et al. |
| 2012/0175599 | A1 | 7/2012 | Yokoyama et al. |
| 2015/0105564 | A1 | 4/2015 | Adachi et al. |
| 2016/0181545 | A1 | 6/2016 | Stoessel et al. |
| 2016/0329512 | A1 | 11/2016 | Nishide et al. |
| 2017/0256720 | A1 | 9/2017 | Adachi et al. |

FOREIGN PATENT DOCUMENTS

| | | | | |
|---|---|---|---|---|
| EP | 2851408 | A1 | 3/2015 | |
| EP | 2980876 | A1 | 2/2016 | |
| EP | 2980877 | A1 | 2/2016 | |
| JP | 2010-245063 | A | 10/2010 | |
| JP | 2010-278390 | A | 12/2010 | |
| JP | 2011-071459 | A | 4/2011 | |
| JP | 2011-100943 | A | 5/2011 | |
| JP | 2014-0965572 | * | 5/2014 | ............ C09K 11/06 |
| JP | 2014-135466 | A | 7/2014 | |
| JP | 2014-214055 | * | 10/2014 | ............ C09K 11/06 |
| JP | 2015-053476 | A | 3/2015 | |
| WO | 2014/128945 | A1 | 8/2014 | |
| WO | 2014/157610 | A1 | 10/2014 | |
| WO | 2014/157619 | A1 | 10/2014 | |
| WO | 2014/194971 | A1 | 12/2014 | |

OTHER PUBLICATIONS

Supplementary European Search Report dated Jul. 13, 2018, issued for the European patent application No. 16768508.0.
Chil Won Lee et al, "Systematic Control of Photophysical Properties of Host Materials for High Quantum Efficiency above 25% in Green Thermally Activated Delayed Fluorescent Devices", Appl.Mater. Interfaces Jan. 22, 2015, 7, pp. 2899-2904. (cited in the ISR).
Jun-ichi Nishide et al, "High-efficiency white organic light-emitting diodes using thermally activated delayed fluorescence", Applied Physics Letters 104, 2004, 233304 (5 pages), (cited in the ISR).
Kim, Bo Seong et al, "Interlayer free hybrid white organic light-emitting diodes with red/blue phosphorescent emitters and a green thermally activated delayed fluorescent emitter", Organic Electronics 21, Feb. 26, 2015, pp. 100-105. (cited in the ISR).
International Search Report dated Jun. 14, 2016, issued for PCT/JP2016/057918.
Office Action issued in corresponding European Patent Application No. EP 16768508.0, dated May 14, 2020.
Office Action issued in corresponding Japanese Patent Application No. JP 2017-508233, dated Jun. 2, 2020.
Office Action issued in corresponding European Patent Application No. EP 16768508.0, dated Jan. 11, 2021.
Office Action issued in corresponding European Patent Application No. EP16768508.0, dated Sep. 27, 2021.

* cited by examiner

MATERIAL FOR ORGANIC ELECTROLUMINESCENT DEVICE, LIGHT-EMITTING MATERIAL, AND ORGANIC ELECTROLUMINESCENT DEVICE

TECHNICAL FIELD

The present invention relates to materials for an organic electroluminescent device, especially light-emitting materials, suitable for an organic electroluminescent device, which is a preferred self-luminous device for various display devices, and to such organic electroluminescent devices. Specifically, this invention relates to materials for an organic electroluminescent device comprising compounds having a benzonitrile structure, and to organic electroluminescent devices (hereinafter also referred to as organic EL devices) using the materials.

BACKGROUND ART

The organic EL device is a self-luminous device and has been actively studied for their brighter, superior visibility and the ability to display clearer images in comparison with liquid crystal devices.

In an attempt to improve the device luminous efficiency, there have been developed devices that use phosphorescent materials to generate phosphorescence, specifically that make use of the emission from the triplet excitation state. According to the excitation state theory, phosphorescent materials are expected to greatly improve luminous efficiency as much as about four times that of the conventional fluorescence.

In 1993, M. A. Baldo et al. at Princeton University realized 8% external quantum efficiency with a phosphorescent device using an iridium complex.

Devices that use light emission caused by thermally activated delayed fluorescence (TADF) have also been developed. In 2011, Adachi et al. at Kyushu University, National University Corporation realized 5.3% external quantum efficiency with a device using a thermally activated delayed fluorescent material (refer to Non-Patent Document 1, for example).

In an organic electroluminescent device, carriers are injected from each of both electrodes, i.e., positive and negative electrodes to a light-emitting substance to generate a light-emitting substance in an excited state so as to emit light. It is generally said that in the case of a carrier injection type organic EL device, 25% of generated excitons are excited to an excited singlet state and the remaining 75% are excited to an excited triplet state. Accordingly, it is conceivable that utilization of light to be emitted from the excited triplet state, i.e., phosphorescence should provide higher energy use efficiency. However, in the phosphorescence, the excited triplet state has a long lifetime, and hence deactivation of energy occurs through saturation of an excited state and interactions with excitons in an excited triplet state, with the result that a high quantum yield is not obtained in many cases in general.

In view of the foregoing, an organic electroluminescent device utilizing a material which emits delayed fluorescence is conceivable. A certain kind of fluorescent substance emits fluorescence via intersystem crossing or the like leading to energy transition to an excited triplet state and the subsequent reverse intersystem crossing to an excited singlet state through triplet-triplet annihilation or thermal energy absorption. In the organic electroluminescent device, it is considered that the latter material which emits thermally activated delayed fluorescence is particularly useful. In this case, when a delayed fluorescent material is utilized in the organic electroluminescent device, excitons in an excited singlet state emit fluorescence as per normal. On the other hand, excitons in an excited triplet state absorb heat produced from a device and undergo intersystem crossing to an excited singlet to emit fluorescence. The fluorescence in this case is light emission from the excited singlet and hence is light emission at the same wavelength as fluorescence. However, the fluorescence has a longer lifetime of light to be emitted, i.e., a longer emission lifetime than those of normal fluorescence and phosphorescence by virtue of reverse intersystem crossing from an excited triplet state to an excited singlet state, and hence is observed as fluorescence delayed as compared to the normal fluorescence and phosphorescence. This can be defined as delayed fluorescence. Through the use of such thermally activated type exciton transfer mechanism, i.e., through thermal energy absorption after carrier injection, the ratio of a compound in an excited singlet state, which has usually been generated only at a ratio of 25%, can be increased to 25% or more. The use of a compound which emits intense fluorescence and delayed fluorescence even at a low temperature of less than 100° C. results in sufficient intersystem crossing from an excited triplet state to an excited singlet state by means of heat of a device, contributing to emission of delayed fluorescence. Thus, the luminous efficiency is drastically improved (refer to Patent Document 1 and Patent Document 2, for example).

For providing high luminance with an organic EL device that uses an ordinary TADF light-emitting material, it is necessary to perform light emission of the device with a high current density, but there may be often a problem of roll-off phenomenon, in which the efficiency is lowered with the increase of the current density. For suppressing the roll-off phenomenon, it is necessary to improve the carrier balance, and to suppress the triplet-triplet annihilation and the singlet-triplet annihilation. However, the ordinary materials cannot effectively suppress the roll-off phenomenon.

The compound of the general formula (X) below is proposed as compounds having a nitrile structure (refer to Patent Document 3, for example).

[Chemical Formula 1]

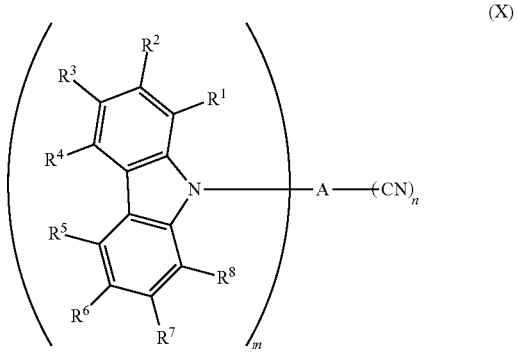

However, there is only a disclosure of the use of the compound only for a host material of a phosphorescent device, but there is no disclosure or suggestion about light emission of the compound itself (dopant material). There is also no disclosure or suggestion about delayed fluorescence, and there is not disclosure or suggestion about suppression of the roll-off phenomenon.

The compound of the general formula (Y) below is proposed as dicyanobenzene derivatives (refer to Patent Document 4, for example).

[Chemical Formula 2]

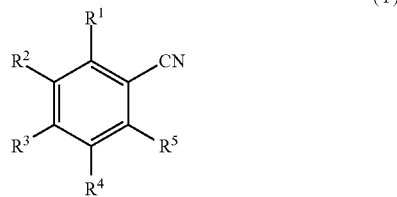

(Y)

However, there is no disclosure about the utilization of the compound as a host material, and even in the case where the compound is used as a dopant material, the roll-off phenomenon cannot be effectively suppressed.

In order to improve characteristics of the organic EL device, it has been desired to develop a material for the organic EL device (the organic compound) that excels in electron injection/transport performances and stability as a thin film, and emits delayed fluorescence.

CITATION LIST

Patent Literature

PTL 1: JP-A-2004-241374
PTL 2: JP-A-2006-024830
PTL 3: JP-A-2009-094486
PTL 4: JP-A-2014-135466

Non Patent Literature

NPL 1: Appl. Phys. Let., 98, 083302 (2011)
NPL 2: Appl. Phys. Let., 101, 093306(2012)
NPL 3: Chem. Commun., 48, 11392(2012)
NPL 4: NATURE 492, 235 (2012)
NPL 5: Organic EL Symposium, the 1st Regular presentation Preprints, 19 (2005)

SUMMARY OF INVENTION

Technical Problem

An object of the present invention is to provide a light-emitting material for a light emitting layer, especially a dopant material or a host material, for a light emitting layer, emitting delayed fluorescence, or a preferred material for a hole blocking layer as a materials for an organic EL device having high efficiency, and to provide, by using the materials, an organic photoluminescent device (hereinafter also referred to as organic PL device), or an organic EL device having high efficiency and high luminance, especially an organic EL device in which the roll-off is suppressed. Physical properties of the material for the organic EL device to be provided by the present invention include (1) high $T_1$ level, wide bandgap between HOMO-LUMO, and deep HOMO level, and comprising a compound having a bipolar transport, (2) stability in a thin-film state, (3) excellent heat resistance.

Solution to Problem

To achieve the above object, the present inventors have noted compounds having a heterocyclic ring structure such as a carbazole ring, and an acridane ring on a benzonitrile structure, and designed and chemically synthesized compounds using, as indexes, a difference between excited triplet energy and excited singlet energy ($\Delta E_{ST}$), and oscillator strength (f) which are obtained by theoretical calculation, further a difference (bandgap) between HOMO level and LUMO level. As a result of actually measuring the emission (PL) spectrums of the chemically synthesized compounds, the present inventors found compounds having a benzonitrile structure and emitting delayed fluorescence. The present inventors produced various test organic electroluminescent devices using these compounds, and the present invention was completed after thorough evaluations of device characteristics.

1) Specifically, the present invention is a light-emitting material comprising a benzonitrile derivative of the following general formula (1).

[Chemical Formula 3]

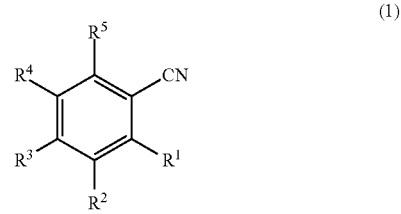

(1)

In the formula, $R^1$ to $R^5$ may be the same or different, and each represent a hydrogen atom, a deuterium atom, a fluorine atom, a chlorine atom, nitro, linear or branched alkyl of 1 to 6 carbon atoms, which may have a substituent, cycloalkyl of 5 to 10 carbon atoms, which may have a substituent, linear or branched alkenyl of 2 to 6 carbon atoms, which may have a substituent, linear or branched alkyloxy of 1 to 6 carbon atoms, which may have a substituent, cycloalkyloxy of 5 to 10 carbon atoms, which may have a substituent, a substituted or unsubstituted aromatic hydrocarbon group, a substituted or unsubstituted aromatic heterocyclic group, a substituted or unsubstituted condensed polycyclic aromatic group, a substituted or unsubstituted aryloxy group, or a disubstituted amino group substituted with a group selected from an aromatic hydrocarbon group, an aromatic heterocyclic group, and a condensed polycyclic aromatic group, and may bind to each other via a single bond, substituted or unsubstituted methylene, an oxygen atom, or a sulfur atom, to form a ring, provided that at least one of $R^1$ to $R^5$ represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group.

2) The present invention is the light-emitting material according to 1), wherein the at least one of $R^1$ to $R^5$ of the general formula (1) is a group selected from a substituted or unsubstituted aromatic heterocyclic group, and a disubstituted amino group substituted with a group selected from an aromatic hydrocarbon group, an aromatic heterocyclic group, and a condensed polycyclic aromatic group.

3) The present invention is the light-emitting material according to 2), wherein the at least one of $R^1$ to $R^5$ of the general formula (1) is a substituted or unsubstituted aromatic heterocyclic group.

4) The present invention is the light-emitting material according to 3), wherein the at least one of $R^1$ to $R^5$ of the general formula (1) is a substituted or unsubstituted nitrogen-containing aromatic heterocyclic group.

5) The present invention is the light-emitting material according to 4), wherein the at least one of $R^1$ to $R^5$ of the general formula (1) is a monovalent group selected from substituted or unsubstituted phenoxazinyl, substituted or unsubstituted phenothiazinyl, substituted or unsubstituted acridinyl, substituted or unsubstituted phenazinyl, substituted or unsubstituted carbazolyl, and substituted or unsubstituted carbolinyl.

6) The present invention is the light-emitting material according to 1), wherein $R^2$ of the general formula (1) is a group selected from a substituted or unsubstituted aromatic hydrocarbon group, a substituted or unsubstituted aromatic heterocyclic group, a substituted or unsubstituted condensed polycyclic aromatic group, and a disubstituted amino group substituted with a group selected from an aromatic hydrocarbon group, an aromatic heterocyclic group, and a condensed polycyclic aromatic group.

7) The present invention is the light-emitting material according to 1), wherein $R^3$ of the general formula (1) is a group selected from a substituted or unsubstituted aromatic hydrocarbon group, a substituted or unsubstituted aromatic heterocyclic group, a substituted or unsubstituted condensed polycyclic aromatic group, and a disubstituted amino group substituted with a group selected from an aromatic hydrocarbon group, an aromatic heterocyclic group, and a condensed polycyclic aromatic group.

8. The present invention is the light-emitting material according to 1), wherein $R^2$ and $R^3$ of the general formula (1) is a group selected from a substituted or unsubstituted aromatic hydrocarbon group, a substituted or unsubstituted aromatic heterocyclic group, a substituted or unsubstituted condensed polycyclic aromatic group, and a disubstituted amino group substituted with a group selected from an aromatic hydrocarbon group, an aromatic heterocyclic group, and a condensed polycyclic aromatic group.

9) The present invention is the light-emitting material according to 1), wherein $R^2$, $R^3$ and $R^4$ of the general formula (1) is a group selected from a substituted or unsubstituted aromatic hydrocarbon group, a substituted or unsubstituted aromatic heterocyclic group, a substituted or unsubstituted condensed polycyclic aromatic group, and a disubstituted amino group substituted with a group selected from an aromatic hydrocarbon group, an aromatic heterocyclic group, and a condensed polycyclic aromatic group.

10) The present invention is the light-emitting material according to 1), wherein the light-emitting material emits delayed fluorescence.

11) The present invention is an organic EL device containing a pair of electrodes and one layer or plural layers including at least a light emitting layer intervening between the electrodes, the light emitting layer containing as a constitutional material thereof the light-emitting material of any one of the items 1) to 9).

12) The present invention is the organic EL device of 11), wherein the light-emitting material of any one of the items 1) to 9) is used as a dopant material of the light emitting layer.

13) The present invention is the organic EL device of 11), wherein the light-emitting material of any one of the items 1) to 9) is used as a host material of the light emitting layer.

14) The present invention is an organic EL device containing a pair of electrodes and plural layers including at least a light emitting layer and a hole blocking layer intervening between the electrodes, the hole blocking layer containing as a constitutional material thereof a benzonitrile derivative of the following general formula (1).

[Chemical Formula 4]

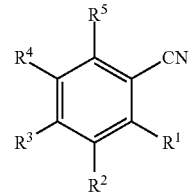

(1)

In the formula, $R^1$ to $R^5$ may be the same or different, and represent a hydrogen atom, a deuterium atom, a fluorine atom, a chlorine atom, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, and may bind to each other via a single bond, substituted or unsubstituted methylene, an oxygen atom, or a sulfur atom to form a ring, provided that at least one of $R^1$ to $R^5$ represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group.

15) The present invention is the organic EL device of 14), wherein the light-emitting material of any one of the items 1) to 9) is used as a constitutional material of the light emitting layer.

16) The present invention is the organic EL device of 14), wherein the light-emitting material of any one of the items 1) to 9) is used as a host material of the light emitting layer.

17) The present invention is the organic electroluminescent device according to 11) or 14), wherein the organic electroluminescent device emits delayed fluorescence.

Specific examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R^1$ to $R^5$ in the general formula (1) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl. These groups may bind to each other via a single bond, substituted or unsubstituted methylene, an oxygen atom, or a sulfur atom to form a ring.

Specific examples of the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R^1$ to $R^5$ in the general formula (1) include a deuterium atom, cyano, nitro; halogen atom, such as a fluorine atom, a chlorine atom, a bromine atom, and an iodine atom; linear or branched alkyloxy of 1 to 6 carbon atoms, such as methyloxy, ethyloxy, and propyloxy; aryloxy, such as phenyloxy and tolyloxy; arylalkyloxy, such as benzyloxy and phenethyloxy; and an aromatic hydrocarbon group or a condensed polycyclic aromatic group, such as phenyl, biphenylyl, terphenylyl, naphthyl, anthracenyl, phenanthrenyl, fluorenyl, indenyl, pyrenyl, perylenyl, fluoranthenyl, and triphenylenyl; an aromatic heterocyclic group, such as pyridyl, pyrimidinyl, triazinyl, thienyl, furyl, pyrrolyl, quinolyl, isoquinolyl, benzofuranyl, benzothienyl, indolyl, carbazolyl, benzoxazolyl, benzothiazolyl, quinoxalinyl, benzimidazolyl, pyrazolyl, dibenzofuranyl, dibenzothienyl, and carbolinyl. These substituents may be further substituted with the exemplified substituents above. These substituents may bind to each other via a single bond, substituted or unsubstituted methylene, an oxygen atom, or a sulfur atom to form a ring.

Specific examples of the "linear or branched alkyloxy of 1 to 6 carbon atoms" or the "cycloalkyloxy of 5 to 10 carbon atoms" in the "linear or branched alkyloxy of 1 to 6 carbon atoms, which may have a substituent" or the "cycloalkyloxy of 5 to 10 carbon atoms, which may have a substituent" represented by $R^1$ to $R^5$ in the general formula (1) include methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy. These groups may bind to each other via a single bond, substituted or unsubstituted methylene, an oxygen atom, or a sulfur atom to form a ring.

These groups may have a substituent. Examples of the substituent include the same groups exemplified as the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R^1$ to $R^5$ in the general formula (1), and possible embodiments may also be the same embodiments as the exemplified embodiments.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R^1$ to $R^5$ in the general formula (1) include phenyl, biphenylyl, terphenylyl, naphthyl, anthracenyl, phenanthrenyl, fluorenyl, indenyl, pyrenyl, perylenyl, fluoranthenyl, triphenylenyl, pyridyl, pyrimidinyl, triazinyl, furyl, pyrrolyl, thienyl, quinolyl, isoquinolyl, benzofuranyl, benzothienyl, indolyl, carbazolyl, benzoxazolyl, benzothiazolyl, quinoxalinyl, benzimidazolyl, pyrazolyl, dibenzoazepinyl, dibenzofuranyl, dibenzothienyl, naphthyridinyl, phenanthrolinyl, phenazinyl, phenoxazinyl, phenocelenazinyl, phenothiazinyl, phenotellurazinyl, phenophosphinazinyl, acridinyl, and carbolinyl.

Specific examples of the "substituent" in the "substituted aromatic hydrocarbon group", the "substituted aromatic heterocyclic group", or the "substituted condensed polycyclic aromatic group" represented by $R^1$ to $R^5$ in the general formula (1) include a deuterium atom, cyano, nitro; halogen atom, such as a fluorine atom, a chlorine atom, a bromine atom, and an iodine atom; linear or branched alkyl of 1 to 6 carbon atoms, such as methyl, ethyl, n-propyl, isopropyl, n-butyl, isobutyl, tert-butyl, n-pentyl, isopentyl, neopentyl, and n-hexyl; linear or branched alkyloxy of 1 to 6 carbon atoms, such as methyloxy, ethyloxy, and propyloxy; linear or branched alkenyl of 2 to 6 carbon atoms, such as vinyl and allyl; aryloxy, such as phenyloxy and tolyloxy; arylalkyloxy, such as benzyloxy and phenethyloxy; an aromatic hydrocarbon group or a condensed polycyclic aromatic group, such as phenyl, biphenylyl, terphenylyl, naphthyl, anthracenyl, phenanthrenyl, fluorenyl, indenyl, pyrenyl, perylenyl, fluoranthenyl, and triphenylenyl; an aromatic heterocyclic group, such as pyridyl, pyrimidinyl, triazinyl, furyl, thienyl, pyrrolyl, quinolyl, isoquinolyl, benzofuranyl, benzothienyl, indolyl, carbazolyl, benzoxazolyl, benzothiazolyl, quinoxalinyl, benzimidazolyl, pyrazolyl, dibenzofuranyl, dibenzothienyl, carbolinyl, phenoxazinyl, phenothiazinyl, acridinyl, and phenazinyl; arylvinyl, such as styryl and naphthylvinyl; acyl, such as acetyl and benzoyl; dialkylamino, such as dimethylamino and diethylamino; a disubstituted amino group substituted with an aromatic hydrocarbon group or a condensed polycyclic aromatic group, such as diphenylamino and dinaphthylamino; diaralkylamino, such as dibenzylamino and diphenethylamino; a disubstituted amino group substituted with an aromatic heterocyclic group, such as dipyridylamino and dithienylamino; dialkenylamino, such as diallylamino; and a disubstituted amino group substituted with a substituent selected from alkyl, an aromatic hydrocarbon group, a condensed polycyclic aromatic group, aralkyl, an aromatic heterocyclic group, and alkenyl. These substituents may be further substituted with the exemplified substituents above.

These substituents may bind to each other via a single bond, substituted or unsubstituted methylene, an oxygen atom, or a sulfur atom to form a ring.

Specific examples of the "aryloxy group" in the "substituted or unsubstituted aryloxy group" represented by $R^1$ to $R^5$ in the general formula (1) include phenyloxy, biphenylyloxy, terphenylyloxy, naphthyloxy, anthracenyloxy, phenanthrenyloxy, fluorenyloxy, indenyloxy, triphenylenyloxy, pyrenyloxy, and perylenyloxy. These groups may bind to each other via a single bond, substituted or unsubstituted methylene, an oxygen atom, or a sulfur atom to form a ring.

These groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $R^1$ to $R^5$ in the general formula (1), and possible embodiments may also be the same embodiments as the exemplified embodiments.

Examples of the "aromatic hydrocarbon group", the "aromatic heterocyclic group", or the "condensed polycyclic aromatic group" in the "disubstituted amino group substituted with a group selected from an aromatic hydrocarbon group, an aromatic heterocyclic group, and a condensed polycyclic aromatic group" represented by $R^1$ to $R^5$ in the general formula (1) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R^1$ to $R^5$ in the general formula (1).

These groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $R^1$ to $R^5$ in the general formula (1), and possible embodiments may also be the same embodiments as the exemplified embodiments.

In the "disubstituted amino group substituted with a group selected from an aromatic hydrocarbon group, an aromatic heterocyclic group, and a condensed polycyclic aromatic group" represented by $R^1$ to $R^5$ in the general formula (1), these groups ($R^1$ to $R^5$) may bind to each other via a single bond, substituted or unsubstituted methylene, an oxygen atom, or a sulfur atom and via the "aromatic hydrocarbon group", the "aromatic heterocyclic group", or the "condensed polycyclic aromatic group" of these groups ($R^1$ to $R^5$) to form a ring.

In the general formula (1), at least one, more preferably at least two, of $R^1$ to $R^5$ is preferably a group selected from a substituted or unsubstituted aromatic heterocyclic group and a disubstituted amino group substituted with a group selected from an aromatic hydrocarbon group, an aromatic heterocyclic group, and a condensed polycyclic aromatic group, more preferably an aromatic heterocyclic group, and particularly preferably a nitrogen-containing aromatic heterocyclic group.

The nitrogen-containing aromatic heterocyclic group is preferably phenoxazinyl, phenothiazinyl, acridinyl, phenazinyl, carbazolyl, or carbolinyl, more preferably phenoxazinyl, phenothiazinyl, carbazolyl, or carbolinyl, and particularly preferably carbazolyl or carbolinyl.

The substituent of these groups is preferably cyano, alkyl of 1 to 4 carbon atoms, an aromatic hydrocarbon group, an aromatic heterocyclic group, or a disubstituted amino group substituted with an aromatic hydrocarbon group, and more preferably cyano, methyl, phenyl, carbazolyl, or diphenylamino.

In the case where at least one of $R^1$ to $R^5$ is carbazolyl, an embodiment where the carbazolyl binds to the benzene ring of the benzonitrile derivative at the 9-position (nitrogen atom) of the carbazolyl is preferred, and in this case, the substituent of the carbazolyl is preferably methyl or phenyl, and the substitution position thereof is preferably the 3-position and/or the 6-position of the carbazolyl.

In the general formula (1), any of $R^2$, $R^3$, and $R^4$ is preferably a group selected from a substituted or unsubstituted aromatic hydrocarbon group, a substituted or unsubstituted aromatic heterocyclic group, a substituted or unsubstituted condensed polycyclic aromatic group, and a disubstituted amino group substituted with a group selected from an aromatic hydrocarbon group, an aromatic heterocyclic group, and a condensed polycyclic aromatic group, and $R^2$ and $R^3$, or $R^2$, $R^3$, and $R^4$ are more preferably a group selected from a substituted or unsubstituted aromatic hydrocarbon group, a substituted or unsubstituted aromatic heterocyclic group, a substituted or unsubstituted condensed polycyclic aromatic group, and a disubstituted amino group substituted with a group selected from an aromatic hydrocarbon group, an aromatic heterocyclic group, and a condensed polycyclic aromatic group.

Accordingly, in the general formula (1), at least $R^3$ is preferably a group selected from a substituted or unsubstituted aromatic hydrocarbon group, a substituted or unsubstituted aromatic heterocyclic group, a substituted or unsubstituted condensed polycyclic aromatic group, and a disubstituted amino group substituted with a group selected from an aromatic hydrocarbon group, an aromatic heterocyclic group, and a condensed polycyclic aromatic group.

$R^1$ or $R^5$ is preferably a hydrogen atom or a deuterium atom, $R^1$ and $R^5$ are more preferably a hydrogen atom or a deuterium atom, and $R^1$ and $R^5$ are particularly preferably a hydrogen atom.

The benzonitrile derivative represented by the general formula (1) that is preferably used in the present invention has a small difference between excited triplet energy and excited single energy ($\Delta E_{ST}$) obtained by theoretical calculation, and a relatively large oscillator strength (f), and therefore has a high luminous efficiency, can emit delayed fluorescence, and is stable in a thin film state.

The benzonitrile derivative represented by the general formula (1) that is preferably used in the present invention has a high $T_1$ level, a wide band gap between HOMO and LUMO, and a deep HOMO level, obtained by theoretical calculation, and therefore has a high capability as a host material of a light emitting layer or a material of a hole blocking layer. The benzonitrile derivative also has a high capability as a dopant material of a light emitting layer emitting blue delayed fluorescence.

The light-emitting material containing the benzonitrile derivative represented by the general formula (1) of the present invention is useful as a constitutional material of a light emitting layer of an organic EL device. The use of the material emitting delayed fluorescence, particularly blue delayed fluorescence, as a light-emitting material (dopant material) of a light emitting layer exhibits a function of drastically enhancing the luminous efficiency.

The light-emitting material containing the benzonitrile derivative represented by the general formula (1) of the present invention is useful as a host material of a light emitting layer of an organic EL device. The production of an organic EL device by using the material can provide an organic EL device having a high luminous efficiency and a low driving voltage.

The benzonitrile derivative represented by the general formula (1) that is preferably used in the present invention can be used as a constitutional material of an electron transport layer of an organic EL device. The use of the material that has a higher electron injection/transport rate than the ordinary materials has a function that the electron transport efficiency from the electron transport layer to the light emitting layer is enhanced to enhance the luminous efficiency, and simultaneously the driving voltage is lowered to enhance the durability of the organic EL device.

The benzonitrile derivative represented by the general formula (1) that is preferably used in the present invention is useful as a constitutional material of a hole blocking layer of an organic EL device. The use of the material that has an excellent hole blocking capability, excellent electron transportability compared to the ordinary materials, and high stability in a thin film state has a function that a high luminous efficiency is provided, the driving voltage is lowered, the current resistance is improved, and the maximum luminance of the organic EL device is enhanced.

Advantageous Effects of Invention

The benzonitrile derivative represented by the general formula (1) that is preferably used in the present invention is useful as a light-emitting material (dopant material or host material) of a light emitting layer of an organic EL device or a constitutional material of a hole blocking layer thereof, can emit delayed fluorescence, is stable in a thin film state, and excellent in heat resistance. The production of an organic EL device by using the compound can provide an organic EL device that has a high efficiency, a high luminance, and a low driving voltage, and is largely suppressed in the roll-off phenomenon of the luminous efficiency (external quantum efficiency).

DESCRIPTION OF EMBODIMENTS

Figure 1:
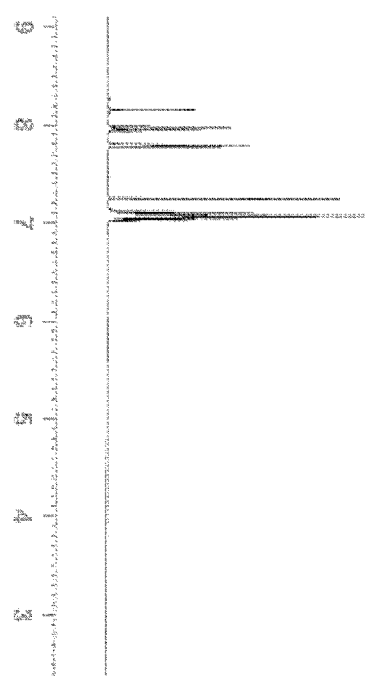
FIG. 1 is a $^1$H-NMR chart of the compound (Compound 5) of Example 1 of the present invention.

The benzonitrile derivative represented by the general formula (1) can be synthesized, for example, in the following manner. In the presence of a base, benzonitrile substituted with halogen, such as fluorine, and an amine compound, such as a nitrogen-containing heterocyclic compound are subjected to condensation reaction, such as Buchwald-Hartwig reaction, so as to synthesize the benzonitrile derivative.

Specific examples of preferred compounds of the benzonitrile derivative represented by the general formula (1) are shown below, but the present invention is not limited to the compounds.

[Chemical Formula 5]

(Compound 1)

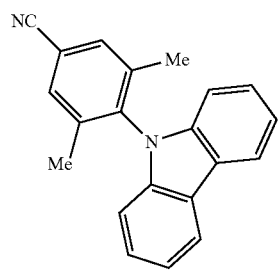

[Chemical Formula 6]

(Compound 2)

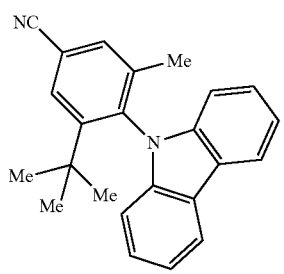

[Chemical Formula 7]

(Compound 3)

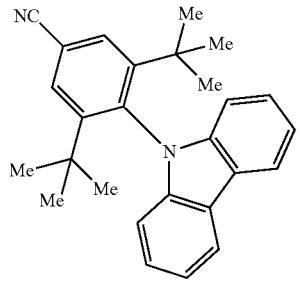

[Chemical Formula 8]

(Compound 4)

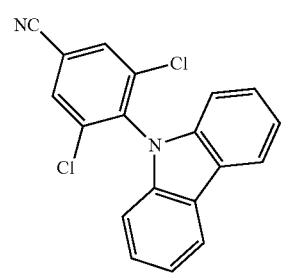

[Chemical Formula 9]

(Compound 5)

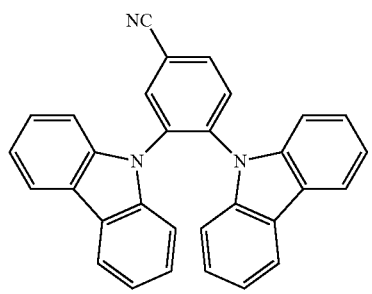

[Chemical Formula 10]

(Compound 6)

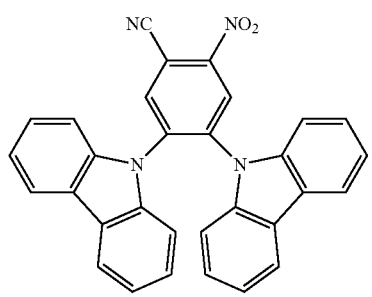

[Chemical Formula 11]

(Compound 7)

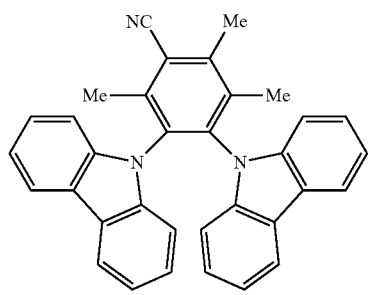

-continued
[Chemical Formula 12]
(Compound 8)
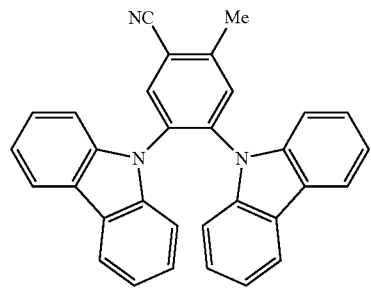
[Chemical Formula 13]
(Compound 9)
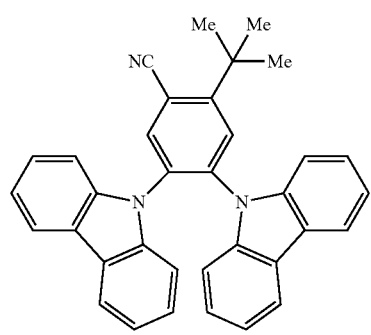
[Chemical Formula 14]
(Compound 10)
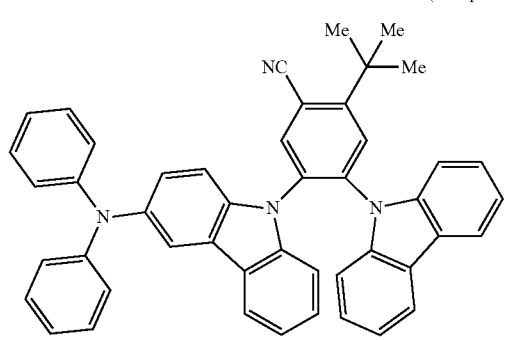
[Chemical Formula 15]
(Compound 11)
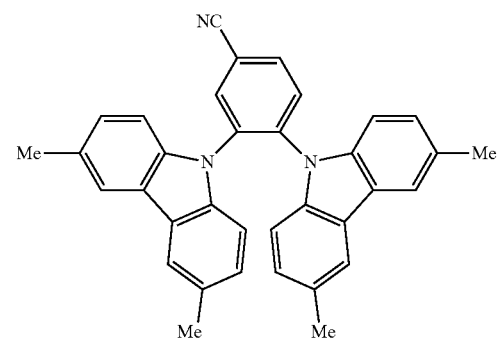
-continued
[Chemical Formula 16]
(Compound 12)
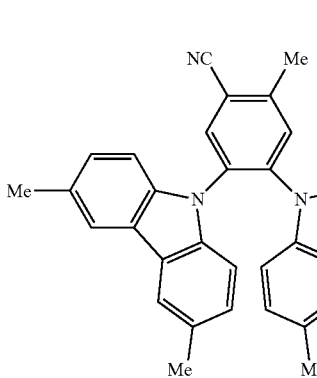
[Chemical Formula 17]
(Compound 13)
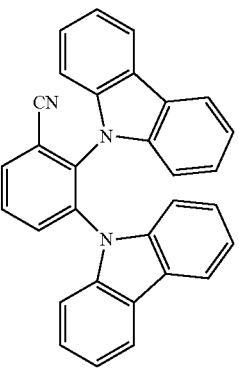
[Chemical Formula 18]
(Compound 14)
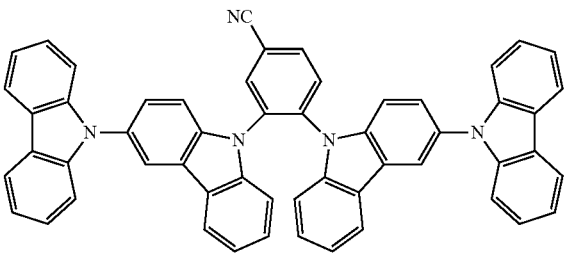
[Chemical Formula 19]
(Compound 15)

-continued
[Chemical Formula 20]
(Compound 16)
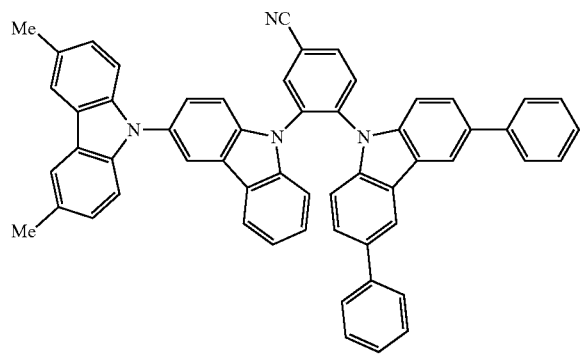
[Chemical Formula 21]
(Compound 17)
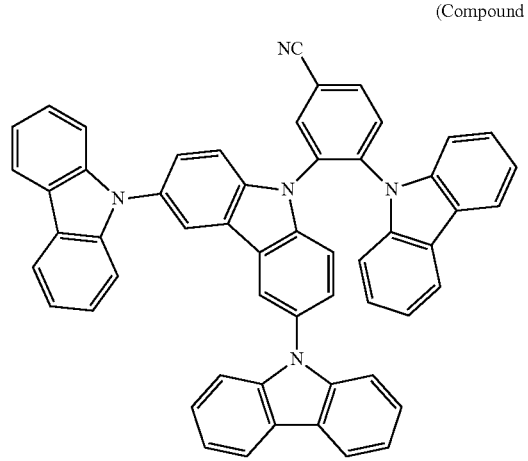
[Chemical Formula 22]
(Compound 18)
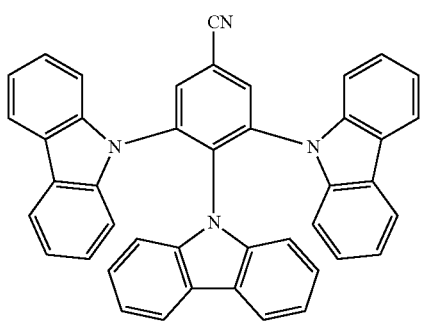
[Chemical Formula 23]
(Compound 19)
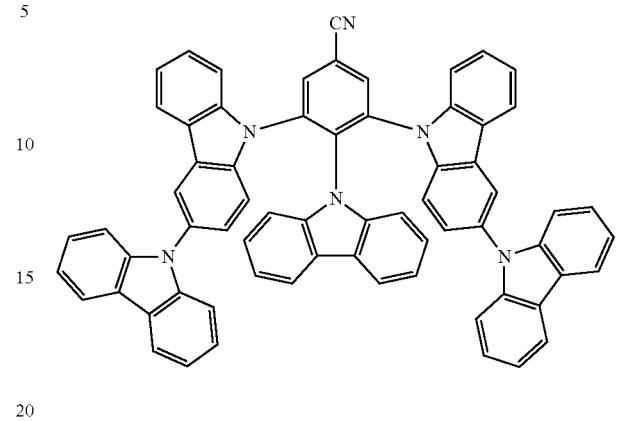
[Chemical Formula 24]
(Compound 20)
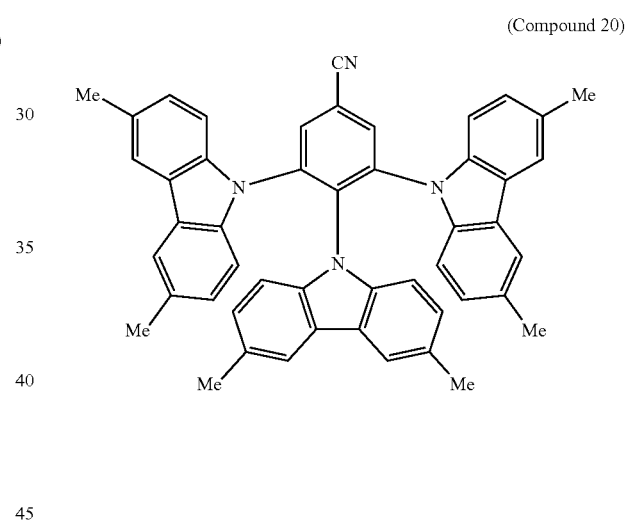
[Chemical Formula 25]
(Compound 21)
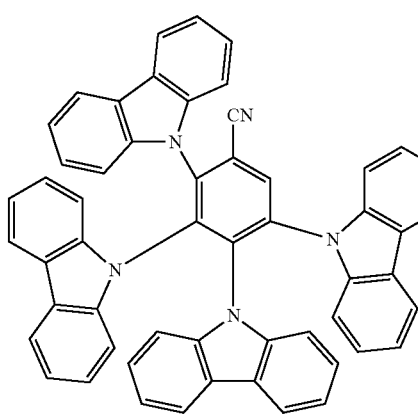

[Chemical Formula 26]
(Compound 22)
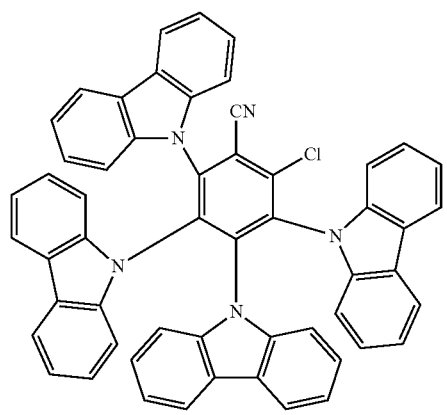
[Chemical Formula 27]
(Compound 23)
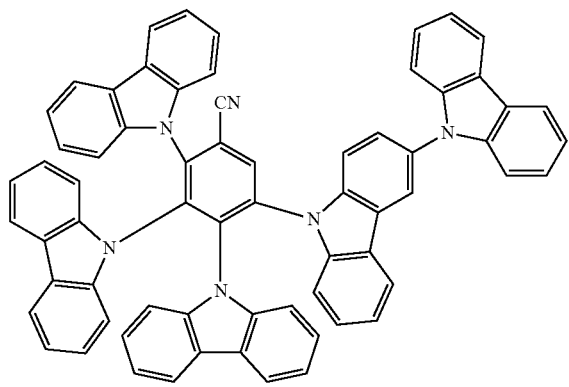
[Chemical Formula 28]
(Compound 24)
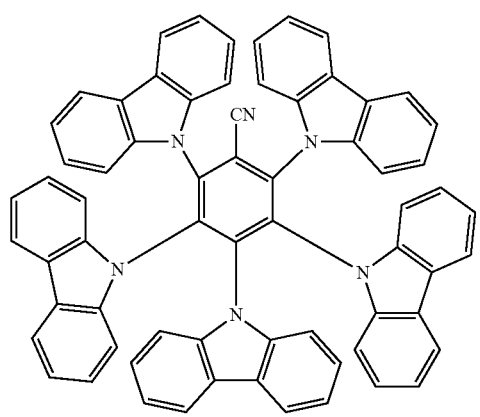
[Chemical Formula 29]
(Compound 25)
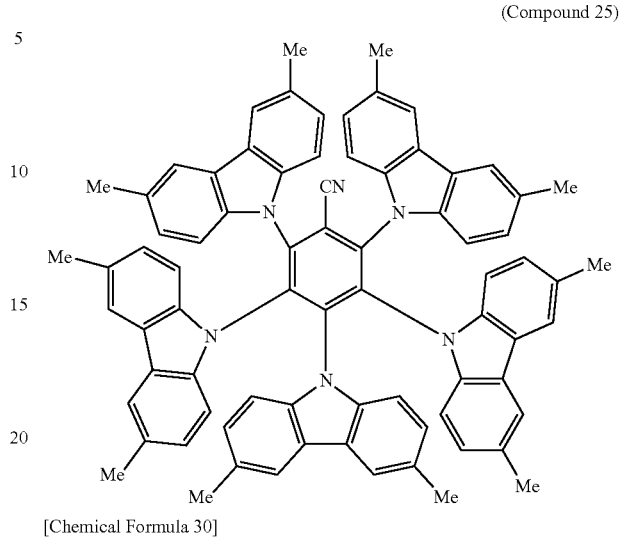
[Chemical Formula 30]
(Compound 26)
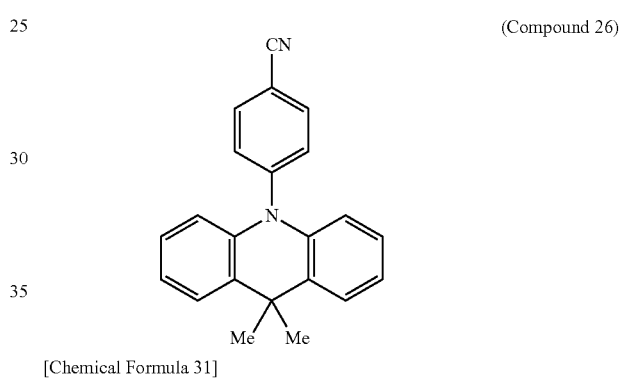
[Chemical Formula 31]
(Compound 27)
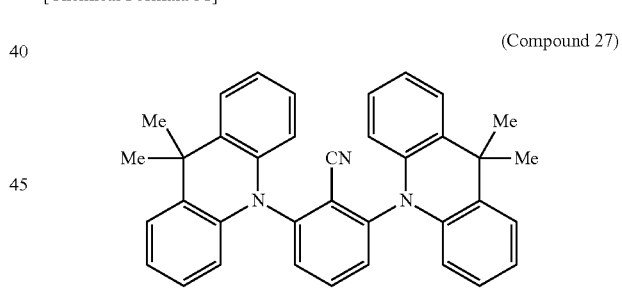
[Chemical Formula 32]
(Compound 28)
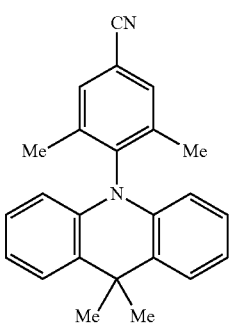

-continued
[Chemical Formula 33]
(Compound 29)
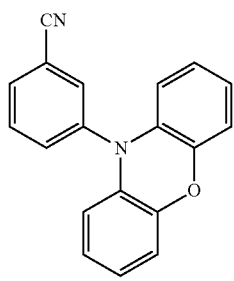
[Chemical Formula 34]
(Compound 30)
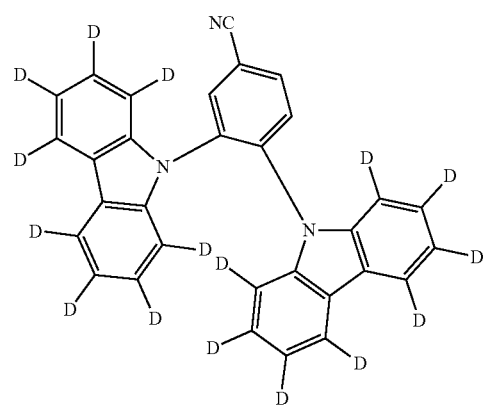
[Chemical Formula 35]
(Compound 31)
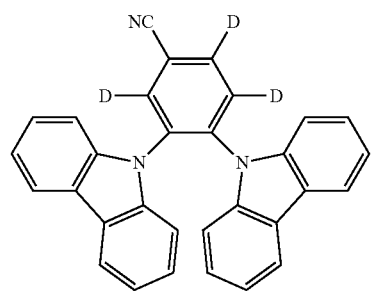
[Chemical Formula 36]
(Compound 32)
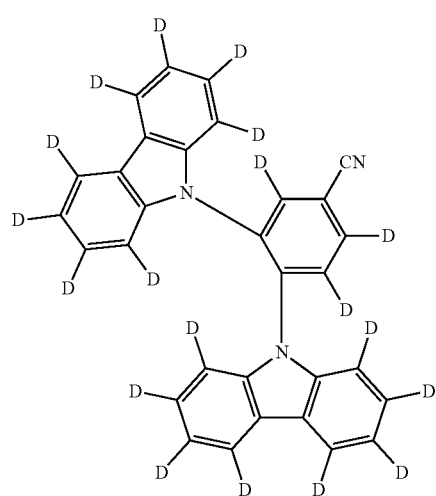
-continued
[Chemical Formula 37]
(Compound 33)
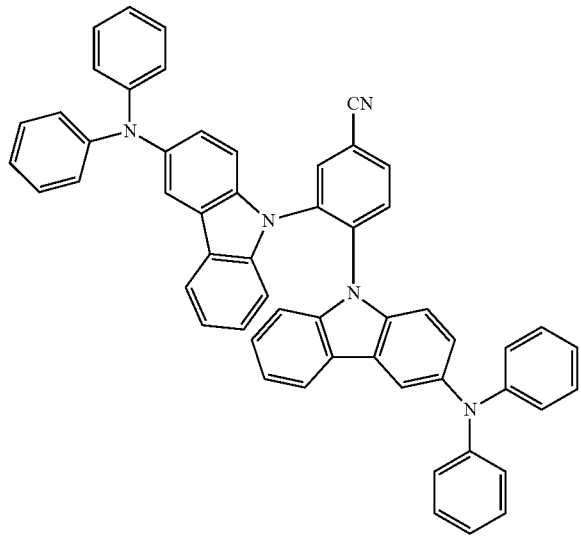
[Chemical Formula 38]
(Compound 34)
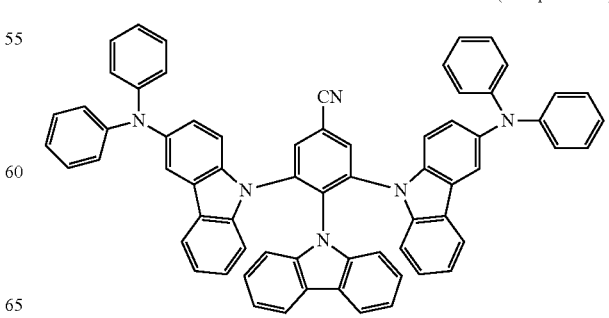
[Chemical Formula 39]
(Compound 35)

[Chemical Formula 40]
(Compound 36)
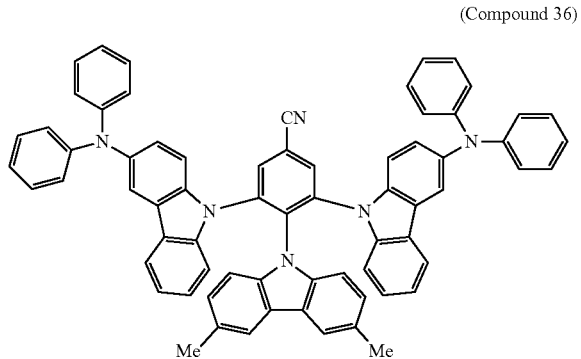
[Chemical Formula 41]
(Compound 37)
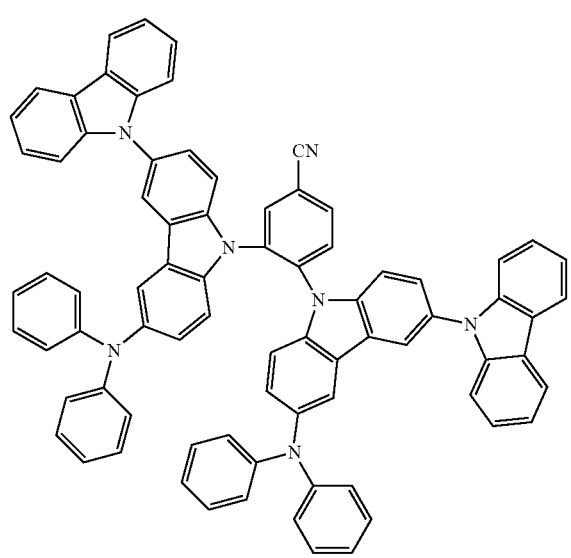
[Chemical Formula 42]
(Compound 38)
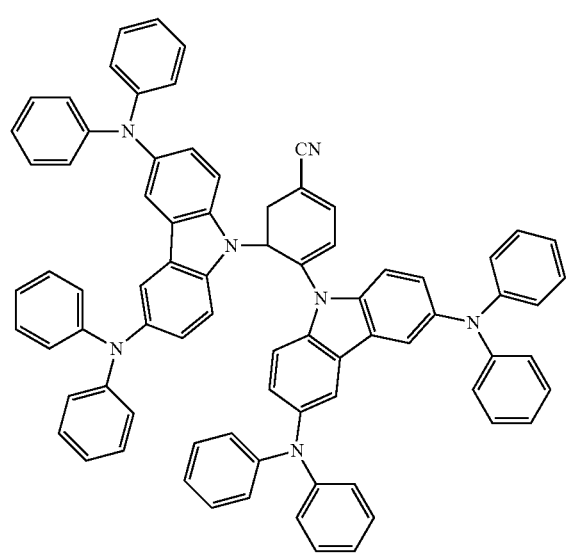
[Chemical Formula 43]
(Compound 39)
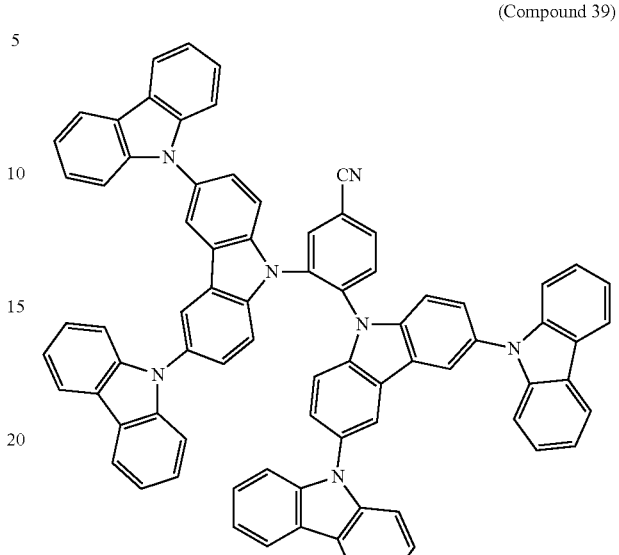
[Chemical Formula 44]
(Compound 40)
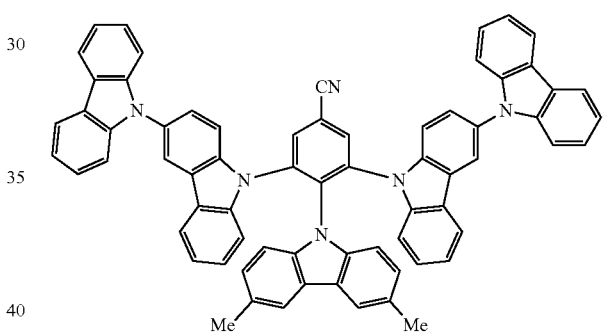
[Chemical Formula 45]
(Compound 41)
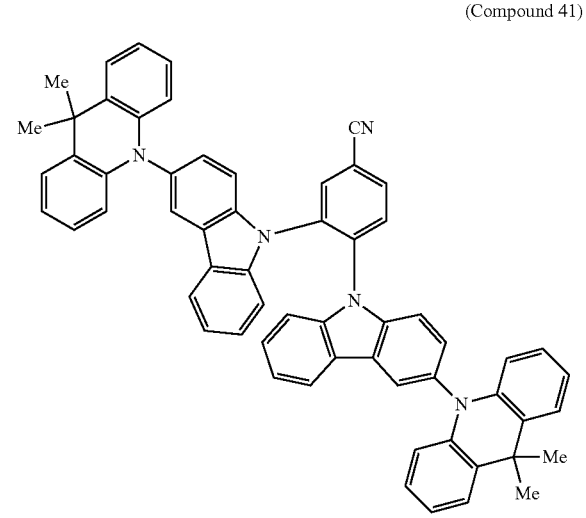

[Chemical Formula 46]
(Compound 42)
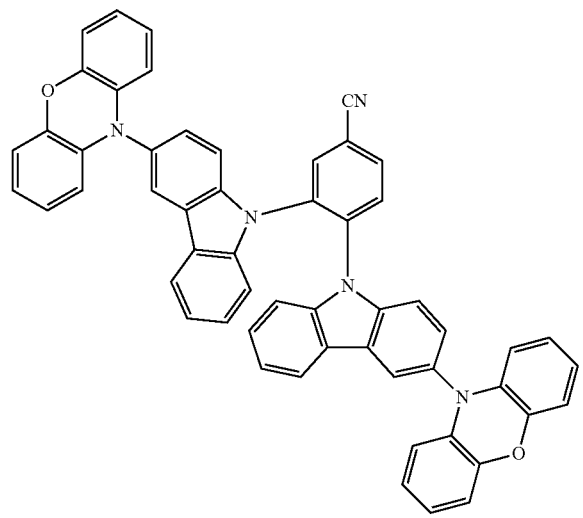
[Chemical Formula 47]
(Compound 43)
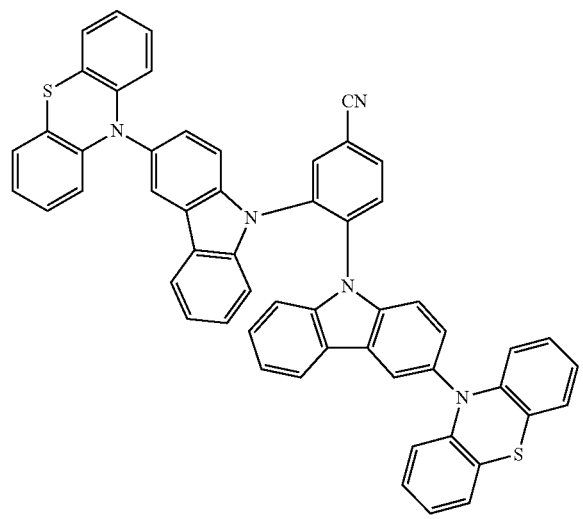
[Chemical Formula 48]
(Compound 44)
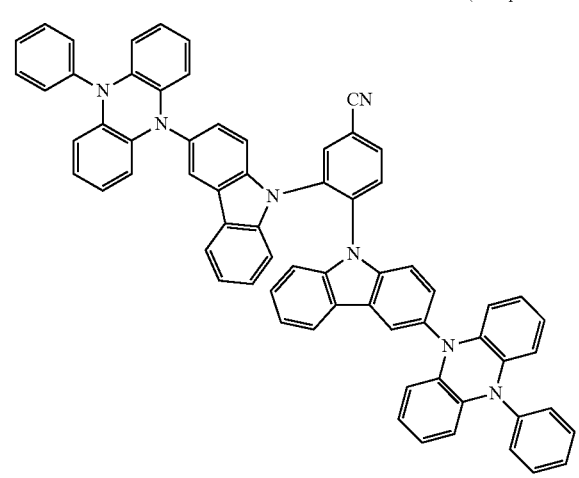
[Chemical Formula 49]
(Compound 45)
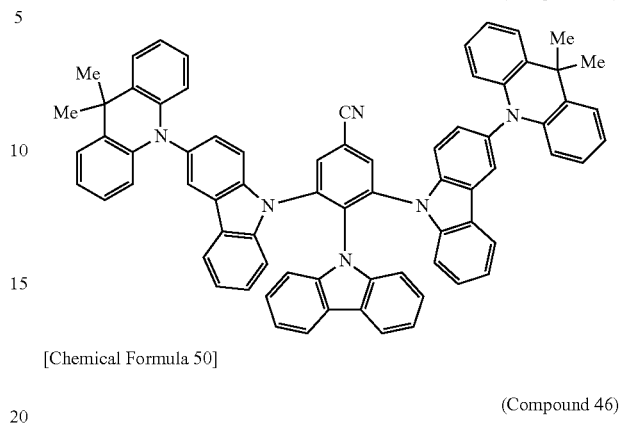
[Chemical Formula 50]
(Compound 46)
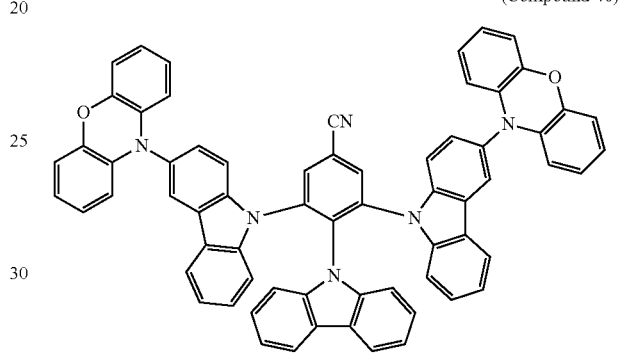
[Chemical Formula 51]
(Compound 47)
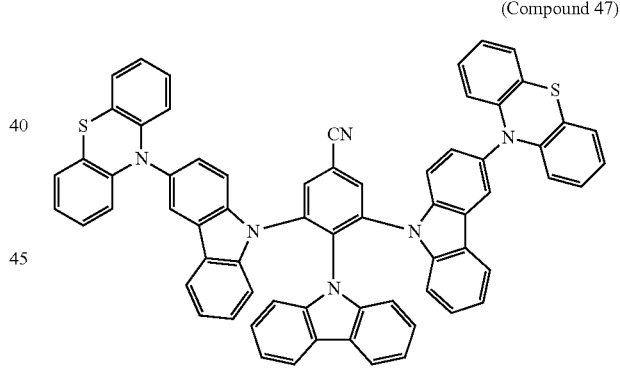
[Chemical Formula 52]
(Compound 48)
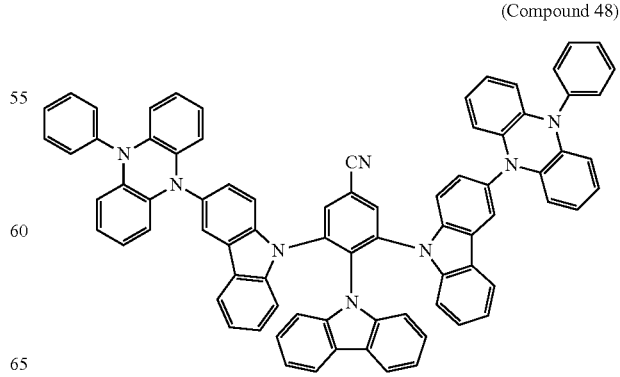

[Chemical Formula 53]
(Compound 49)
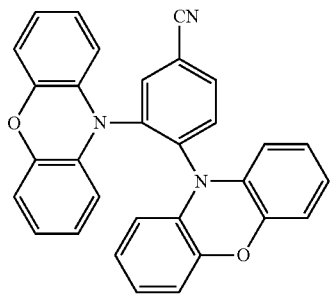
[Chemical Formula 54]
(Compound 50)
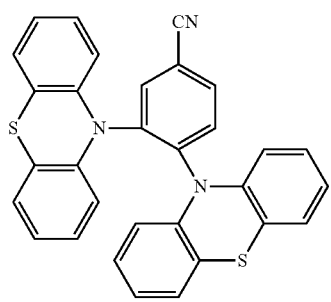
[Chemical Formula 55]
(Compound 51)
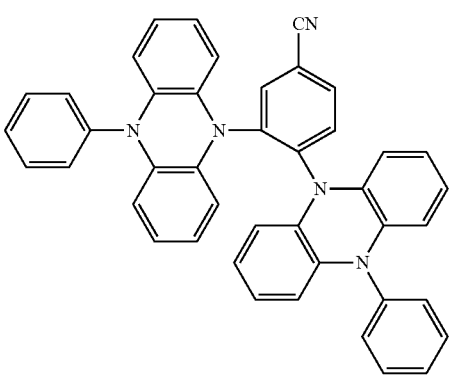
[Chemical Formula 56]
(Compound 52)
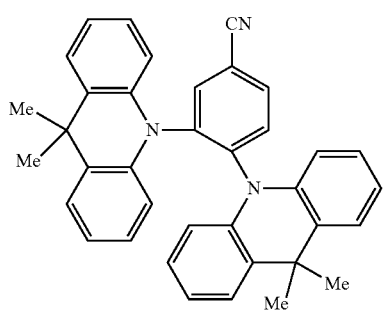
[Chemical Formula 57]
(Compound 53)
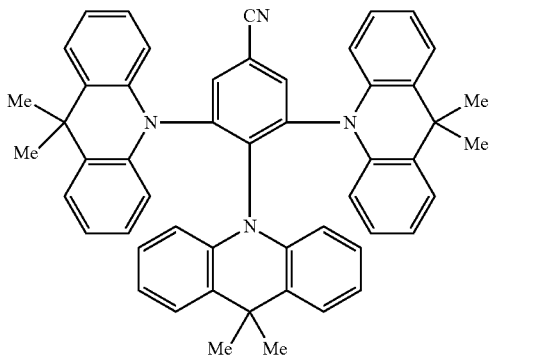
[Chemical Formula 58]
(Compound 54)
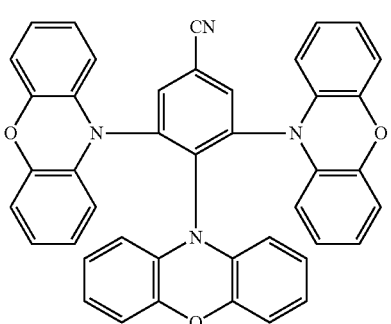
[Chemical Formula 59]
(Compound 55)
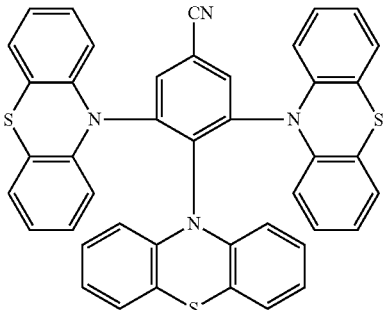
[Chemical Formula 60]
(Compound 56)
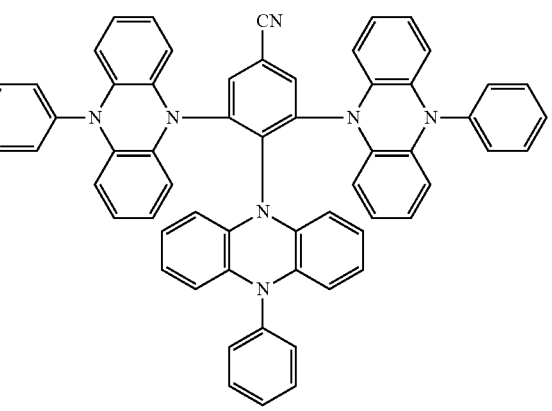

These compounds are purified by methods such as column chromatography, adsorption using, for example, a silica gel, activated carbon, or activated clay, recrystallization or crystallization using a solvent, and a sublimation purification method. The compounds are identified by an NMR analysis.

As a property value thereof, a work function thereof is measured. The work function is an index of the energy level as a material of a light emitting layer or an index of a hole blocking capability.

For the measurement of work function, a 100 nm-thick thin film was fabricated on an ITO substrate, and an atmosphere photoelectron spectrometer (AC-3 produced by Riken Keiki Co., Ltd.) was used.

Examples of the structure of the organic EL device of the present invention include a structure containing an anode, a hole transport layer, a light emitting layer, an electron transport layer, an electron injection layer, and a cathode successively formed on a substrate, optionally with a hole injection layer between the anode and the hole transport layer, an electron blocking layer between the light emitting layer and the hole transport layer, a hole blocking layer between the light emitting layer and the electron transport layer, and an exciton blocking layer on the anode side and/or the cathode side of the light emitting layer. Some of the organic layers in the multilayer structure may be omitted, for example, a single organic layer may serve as the electron injection layer and the electron transport layer, i.e., a structure containing an anode, a hole transport layer, a light emitting layer, an electron transport layer, and a cathode successively formed on a substrate.

Furthermore, two or more organic layers having the same function may be laminated, for example, two layers of the hole transport layers may be laminated, two layers of the light emitting layers may be laminated, and two layers of the electron transport layers may be laminated.

Electrode materials with high work functions such as ITO and gold are used as the anode of the organic EL device of the present invention. Examples of the material used for the hole injection layer of the organic EL device of the present invention can be naphthalenediamine derivatives; starburst-type triphenylamine derivatives; triphenylamine trimers and tetramers such as an arylamine compound having a structure in which three or more triphenylamine structures are joined within the molecule via a single bond or a divalent group that does not contain a heteroatom; accepting heterocyclic compounds such as hexacyano azatriphenylene; and coating-type polymer materials, in addition to porphyrin compounds as represented by copper phthalocyanine. These materials may be formed into a thin film by a vapor deposition method, or other known methods such as a spin coating method and an inkjet method.

Examples of material used for the hole transport layer of the organic EL device of the present invention can be benzidine derivatives such as N,N'-diphenyl-N,N'-di(m-tolyl)-benzidine (TPD), N,N'-diphenyl-N,N'-di(α-naphthyl)-benzidine (NPD), and N,N,N',N'-tetrabiphenylylbenzidine; 1,1-bis[(di-4-tolylamino)phenyl]cyclohexane (TAPC); various triphenylamine trimers and tetramers; and carbazole derivatives, in addition to compounds containing an m-carbazolylphenyl group. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. Examples of material used for the hole injection/transport layer can be coating-type polymer materials such as poly(3,4-ethylenedioxythiophene) (PEDOT)/poly(styrene sulfonate) (PSS). These materials may be formed into a thin-film by a vapor deposition method or other known methods such as a spin coating method and an inkjet method.

In the hole injection layer or the hole transport layer, a p-doped material of trisbromophenylamine hexachloro antimony, a radialene derivative (see, for example, WO 2014/009310), or the like, a polymer compound having a structure of a benzidine derivative, such as TPD, as a partial structure thereof, or the like may be used with the material that is ordinarily used in the layer.

The electron blocking layer used of the organic EL device of the present invention may be a compound having an electron blocking capability, such as a carbazole derivative, such as 4,4',4"-tri(N-carbazolyl)triphenylamine (TCTA), 9,9-bis[4-(carbazol-9-yl)phenyl]fluorene, 1,3-bis(carbazol-9-yl)benzene (mCP), and 2,2-bis(4-carbazol-9-ylphenyl) adamantane (Ad-Cz), a compound having a triphenylsilyl group and a triarylamine structure, represented by 9-[4-(carbazol-9-yl)phenyl]-9-[4-(triphenylsilyl)phenyl]-9H-fluorene, a monoamine compound having high electron blocking property, and various triphenylamine dimers. These compounds each may be individually formed into a film, may be formed into a single layer with another material mixed, or may be formed into a laminated structure containing the individually formed layers, a laminated structure containing the layers with another material mixed, or a laminated structure containing the individually formed layer and the layer with another material mixed. These materials may be formed into a thin film by a vapor deposition method or other known methods such as a spin coating method and an inkjet method.

The light emitting layer used of the organic EL device of the present invention may be a material emitting delayed fluorescence, such as the benzonitrile derivative represented by the general formula (1), PIC-TRZ (see, for example, NPL 1), CC2TA (see, for example, NPL 2), PXZ-TRZ (see, for example, NPL 3), and a CDCB derivative, e.g., 4CzIPN (see, for example, NPL 4), various metal complexes, such as a metal complex of a quinolinol derivative, e.g., tris(8-hydroxyquinoline) aluminum ($Alq_3$), an anthracene derivative, a bisstylylbenzene derivative, a pyrene derivative, an oxazole derivative, a poly-p-phenylenevinylene derivative, and the like. The light emitting layer may be formed of a host material and a dopant material, and in this case, the host material used may be the benzonitrile derivative represented by the general formula (1), mCP, a thiazole derivative, a benzimidazole derivative, a polydialkylfluorene derivative, and the like. The dopant material used may be a material emitting delayed fluorescence, such as the benzonitrile derivative represented by the general formula (1), PIC-TRZ, CC2TA, PXZ-TRZ, and a CDCB derivative, e.g., 4CzIPN, quinacridone, coumarin, rubrene, anthracene, perylene, and derivatives thereof, a benzopyran derivative, a rhodamine derivative, an aminostyryl derivative, and the like. These compounds each may be individually formed into a film, may be formed into a single layer with another material mixed, or may be formed into a laminated structure containing the individually formed layers, a laminated structure containing the layers with another material mixed, or a laminated structure containing the individually formed layer and the layer with another material mixed.

A phosphorescent light-emitting material can also be used as the light-emitting material. The phosphorescent light-emitting material used may be a phosphorescent light-emitting material of a metal complex of iridium, platinum, or the like. A green phosphorescent light-emitting material, such as $Ir(ppy)_3$, a blue phosphorescent light-emitting material, such as FIrpic and FIr6, a red phosphorescent light-emitting material, such as $Btp_2Ir(acac)$ and $Ir(piq)_3$, may be used, and the host material used therefor is preferably the benzonitrile derivative represented by the general formula (1), and in addition, a heterocyclic compound having an indole ring as a partial structure of a condensed ring, and as a hole injection/transport host material, a carbazole derivative, such as 4,4'-di(N-carbazolyl)biphenyl (CBP), TCTA, and mCP, may be used. The electron transport host material used may be p-bis(triphenylsilyl)benzene (UGH2), 2,2',2"-(1,3,5-phenylene)-tris(1-phenyl-1H-benzimidazole) (TPBI), and the like, and thereby an organic EL device having high performance can be produced. These compounds each may be individually formed into a film, may be formed into a single layer with another material mixed, or may be formed into a laminated structure containing the individually formed layers, a laminated structure containing the layers with another material mixed, or a laminated structure containing the individually formed layer and the layer with another material mixed.

In order to avoid concentration quenching, the doping of the host material with the phosphorescent light-emitting material is preferably made by co-evaporation in a range of 1 to 30% by weight with respect to the total light emitting layer.

These materials may be formed into a thin film by a vapor deposition method or other known methods such as a spin coating method and an inkjet method.

A device may be produced to have a structure containing a light emitting layer produced by using the light-emitting material containing the compound of the present invention having laminated adjacently thereon a light emitting layer produced by using a compound having a different work function as a host material (see, for example, NPL 5).

The hole blocking layer used of the organic EL device of the present invention may be the benzonitrile derivative represented by the general formula (1), and also may be a phenanthroline derivative, e.g., bathocuproine (BCP), a metal complex of a quinolinol derivative, such as aluminum (III) bis(2-methyl-8-quinolinato)-4-phenylphoenolate (BAlq), a dibenzothiophene derivative, such as 2,8-bis(diphenylphosphoryl)dibenzo[b,d]thiophene (PPT), and hole blocking compounds, such as various kinds of a rare earth complex, an oxazole derivative, a triazole derivative, and a triazine derivative. These materials may also serve as the material of the electron transport layer. These compounds each may be individually formed into a film, may be formed into a single layer with another material mixed, or may be formed into a laminated structure containing the individually formed layers, a laminated structure containing the layers with another material mixed, or a laminated structure containing the individually formed layer and the layer with another material mixed. These materials may be formed into a thin film by a vapor deposition method or other known methods such as a spin coating method and an inkjet method.

The electron transport layer used of the organic EL device of the present invention may be the benzonitrile derivative represented by the general formula (1), and also may be various metal complexes, such as a metal complex of a quinolinol derivative, e.g., Alq$_3$ and BAlq, a triazole derivative, a triazine derivative, an oxadiazole derivative, a pyridine derivative, a pyrimidine derivative, a thiadiazole derivative, a benzotriazole derivative, a carbodiimide derivative, a quinoxaline derivative, a pyridoindole derivative, a phenanthroline derivative, a silole derivative, a compound having an anthracene ring structure, and a benzimidazole derivative, such as TPBI. These compounds each may be individually formed into a film, may be formed into a single layer with another material mixed, or may be formed into a laminated structure containing the individually formed layers, a laminated structure containing the layers with another material mixed, or a laminated structure containing the individually formed layer and the layer with another material mixed. These materials may be formed into a thin film by a vapor deposition method or other known methods such as a spin coating method and an inkjet method.

The electron injection layer used of the organic EL device of the present invention may be an alkali metal salt, such as lithium fluoride and cesium fluoride, an alkaline earth metal salt, such as magnesium fluoride, a metal oxide, such as aluminum oxide, and the like, and may be omitted in the preferred selection of the electron transport layer and the cathode.

In the electron injection layer or the electron transport layer, a material that is ordinarily used in the layers having been n-doped with a metal, such as cesium, a triarylphosphine oxide derivative (see, for example, WO 2014/195482), or the like may also be used.

The electrode material of the cathode used of the organic EL device of the present invention may be an electrode material having a low work function, such as aluminum, or an alloy having a lower work function, such as a magnesium-silver alloy, a magnesium-indium alloy, or an aluminum-magnesium alloy.

Specific examples of preferred materials that may be used in the organic EL device of the present invention are shown below, but the materials that may be used in the present invention are not construed as being limited to the following exemplified compounds. The compound that is shown as a material having a particular function may also be used as a material having another function. In the structural formulae of the following exemplified compounds, R and R$_2$ to R$_7$ each independently represent a hydrogen atom or a substituent, and n represents an integer of 3 to 5.

Preferred examples of a compound that may also be used as the host material of the light emitting layer are shown below.

[Chemical Formula 61]

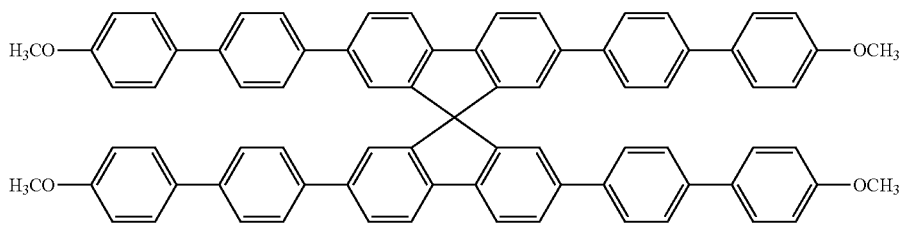

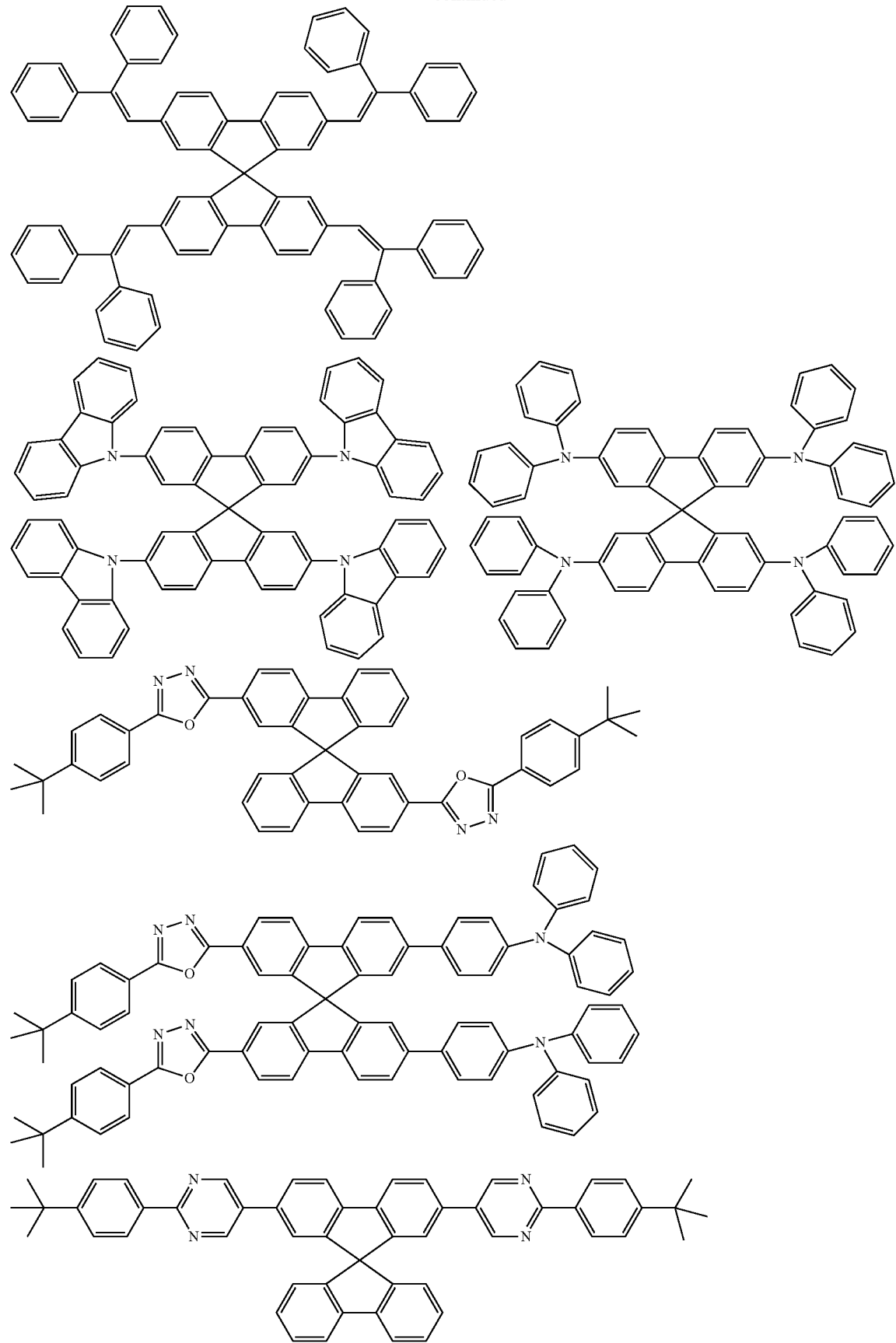

[Chemical Formula 62]
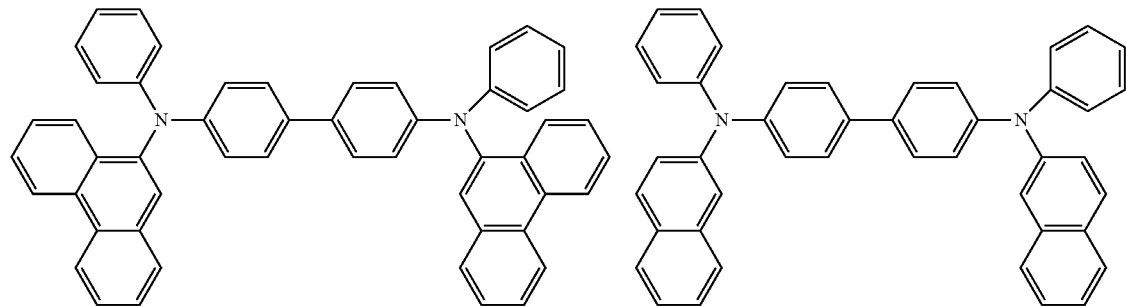
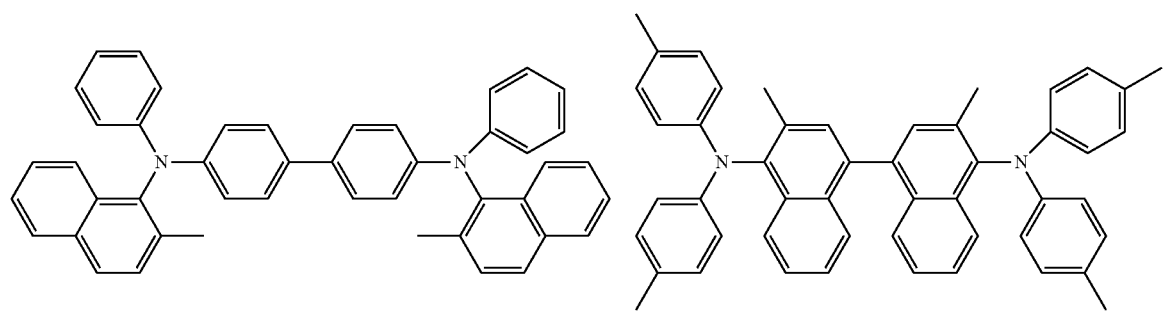
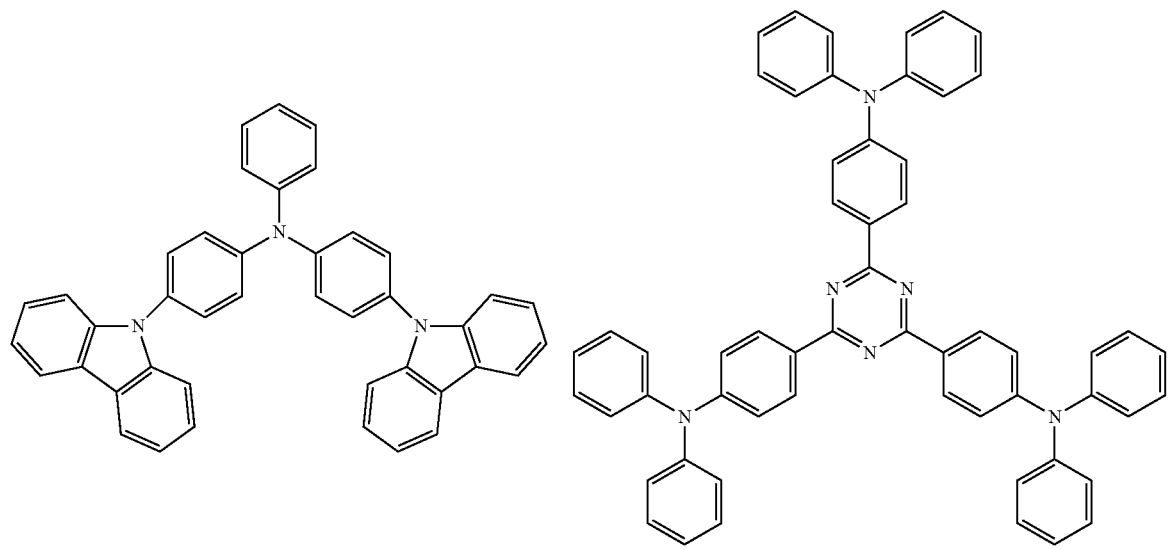

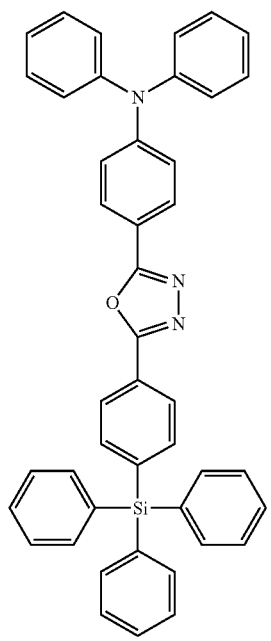
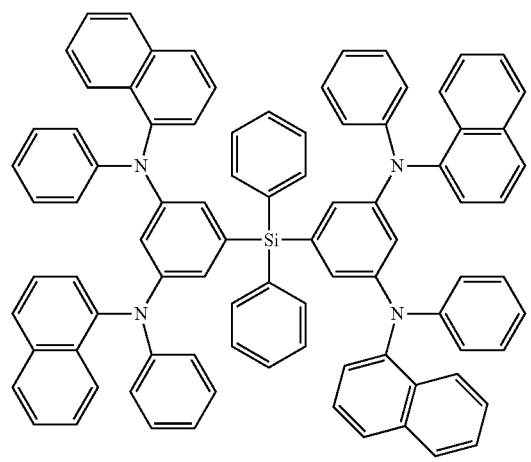
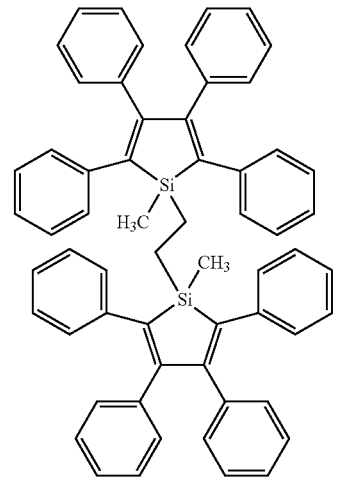
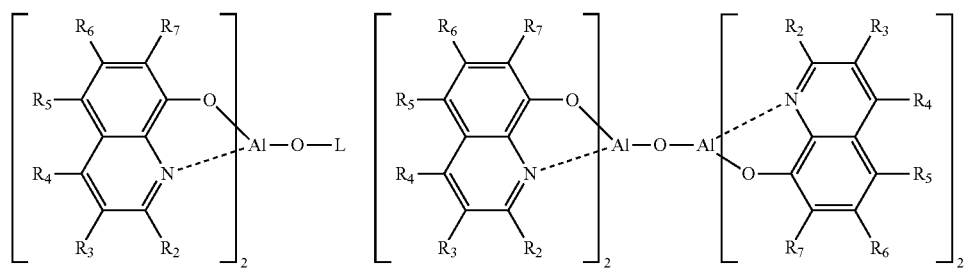
[Chemical Formula 63]
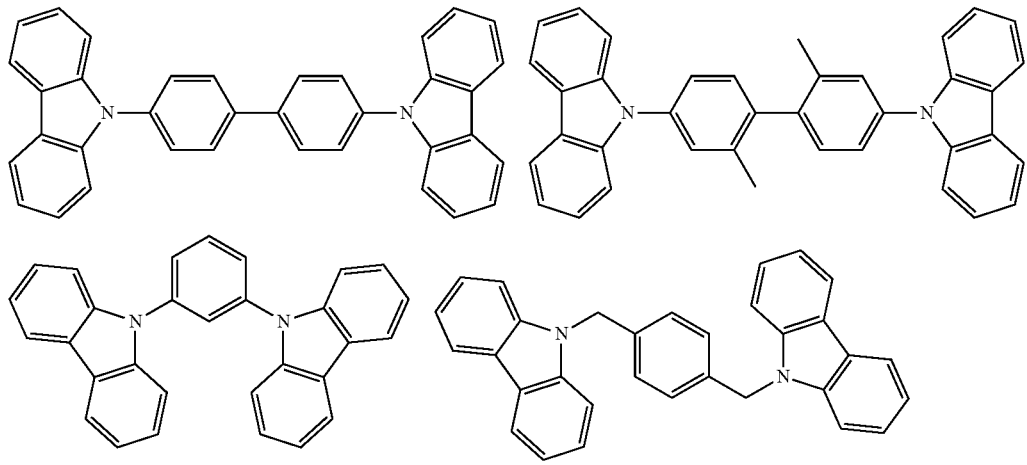

-continued
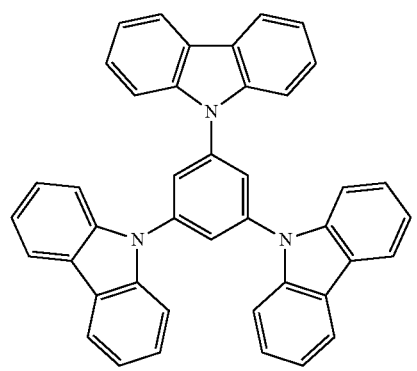
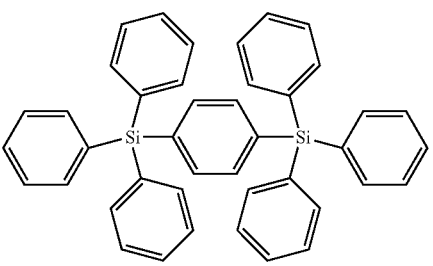
[Chemical Formula 64]
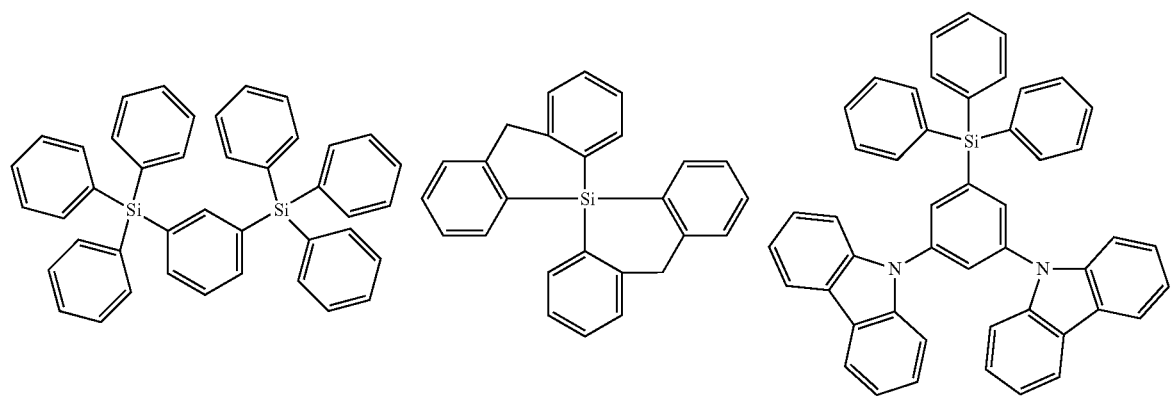
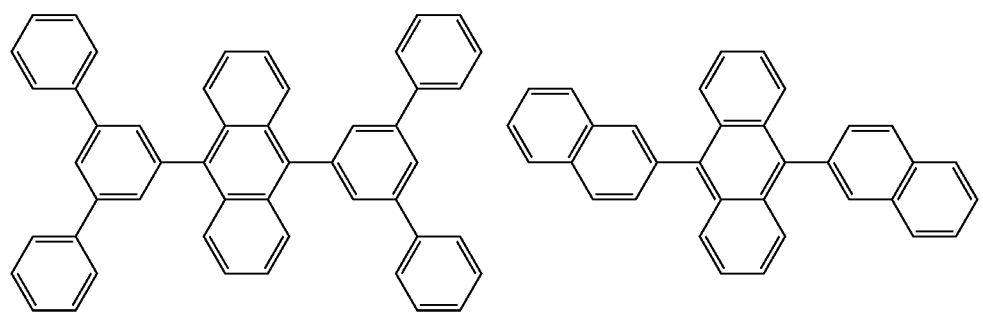
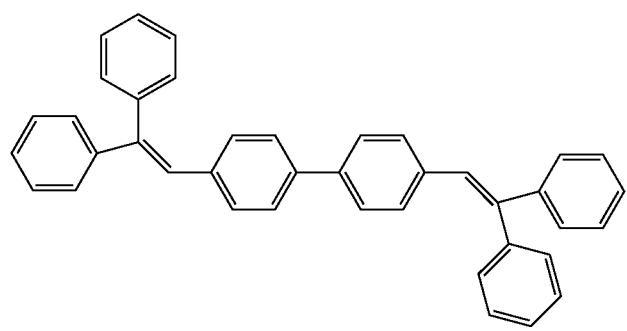

-continued
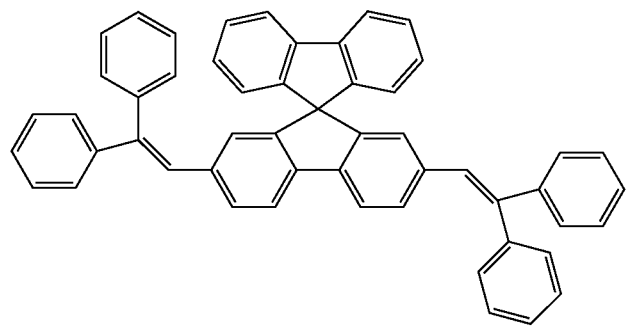
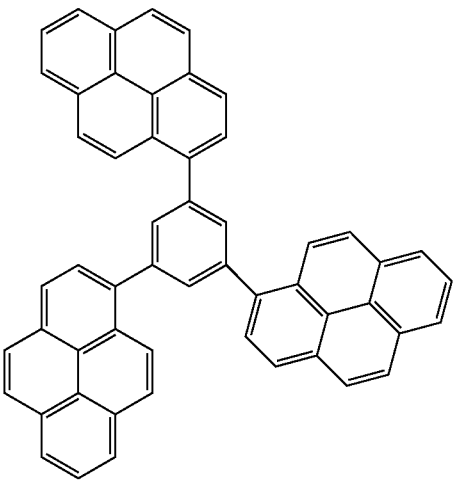
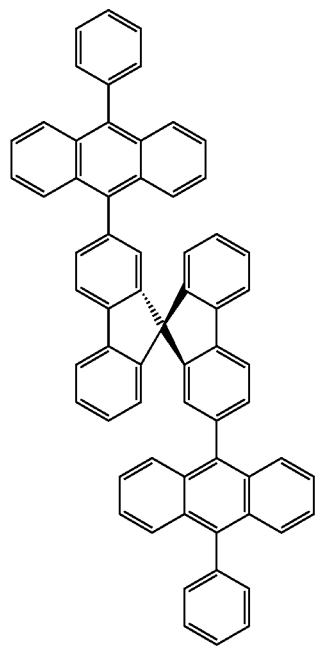
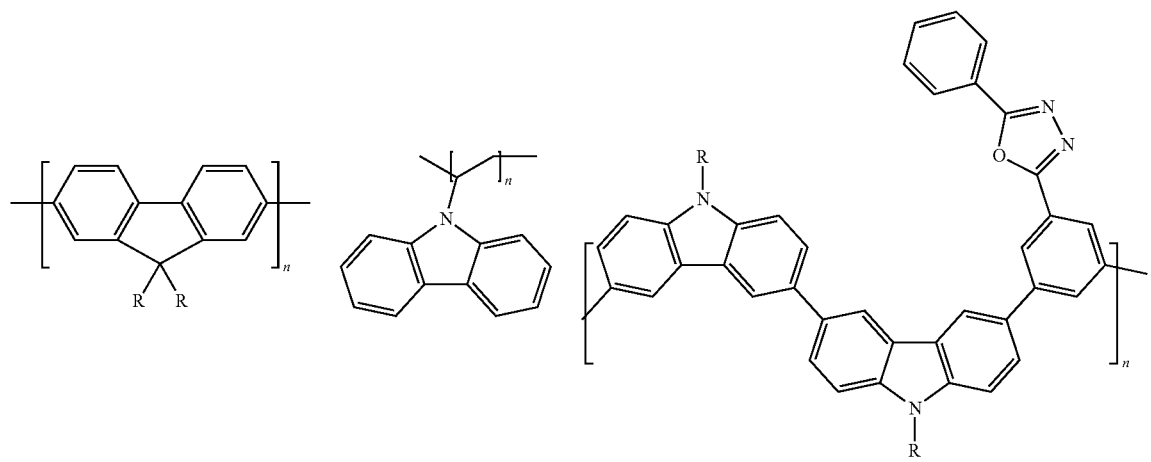

[Chemical Formula 65]
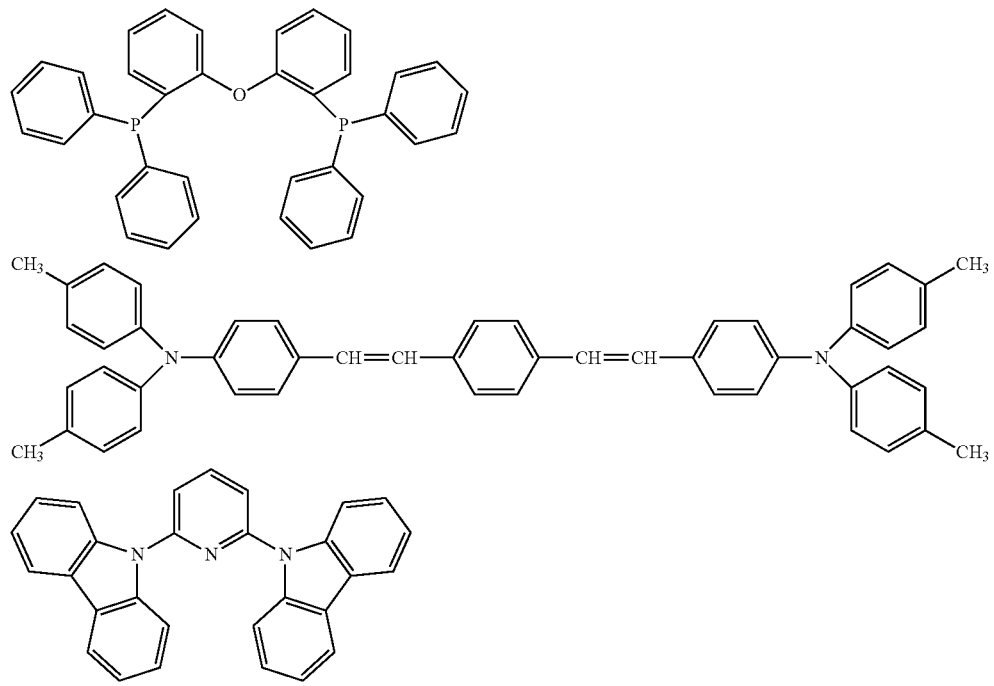
Preferred examples of a compound that may also be used as the material of the hole injection layer are shown below.
[Chemical Formula 66]
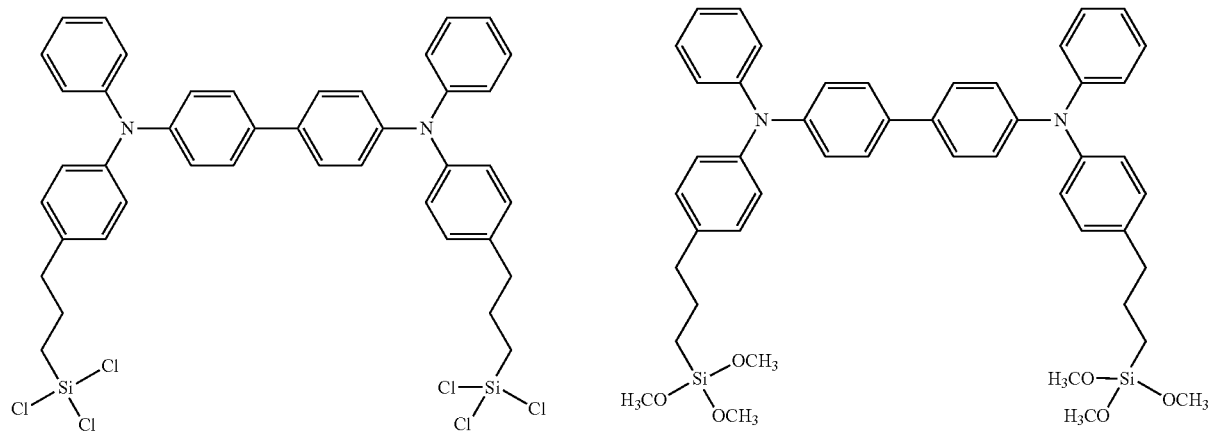
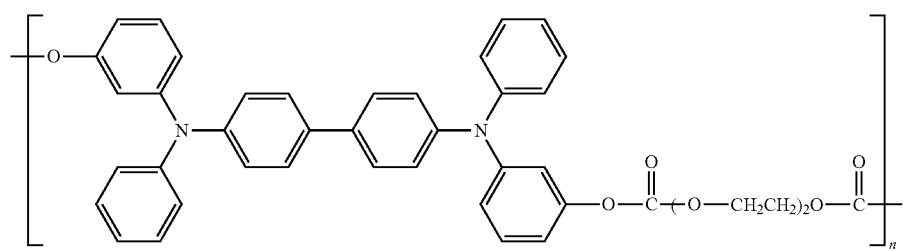

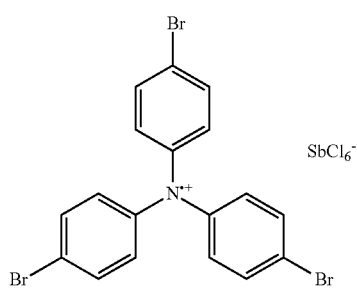
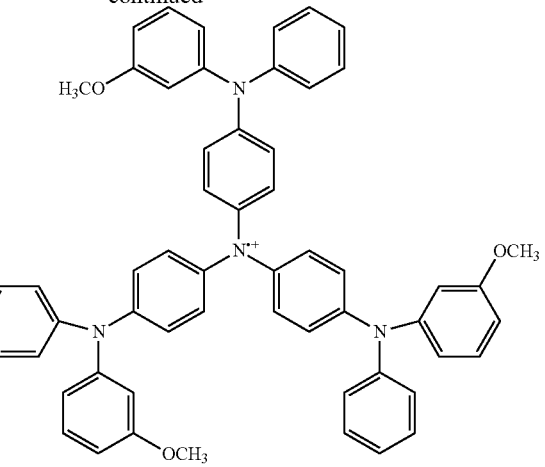
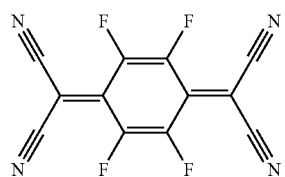
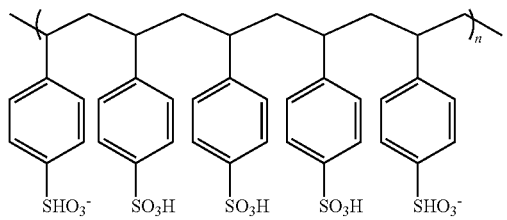
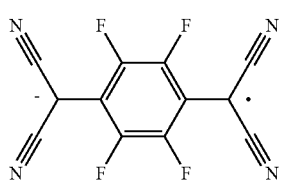
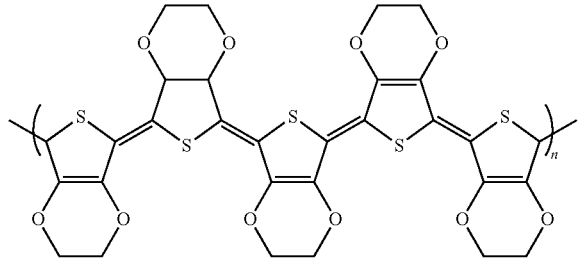
Preferred examples of a compound that may also be used as the material of the hole transport layer are shown below.
[Chemical Formula 67]
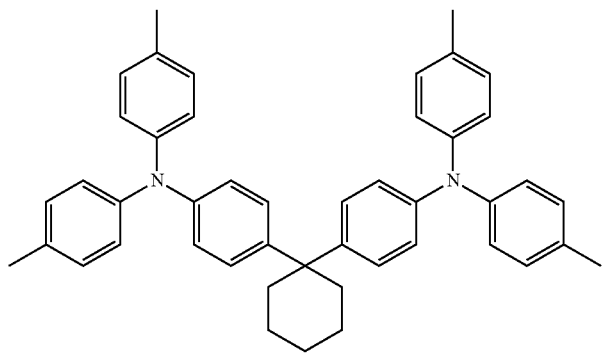
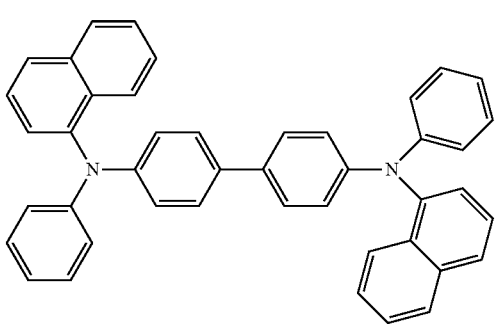

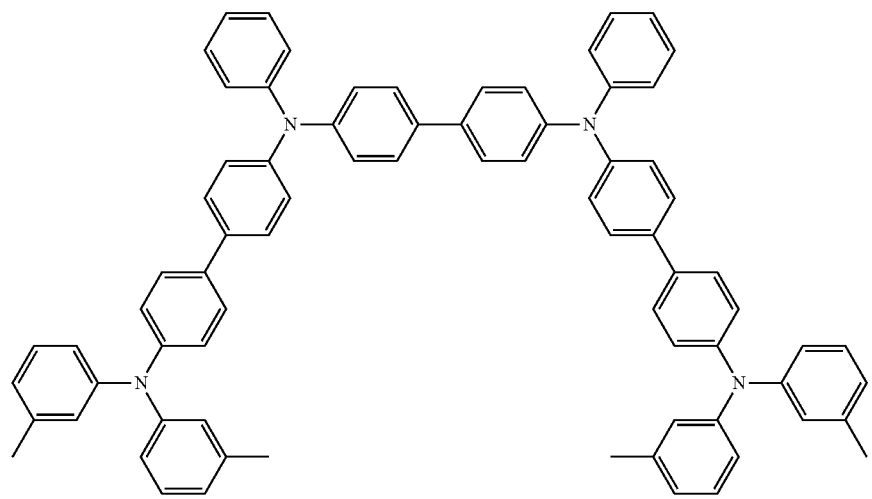
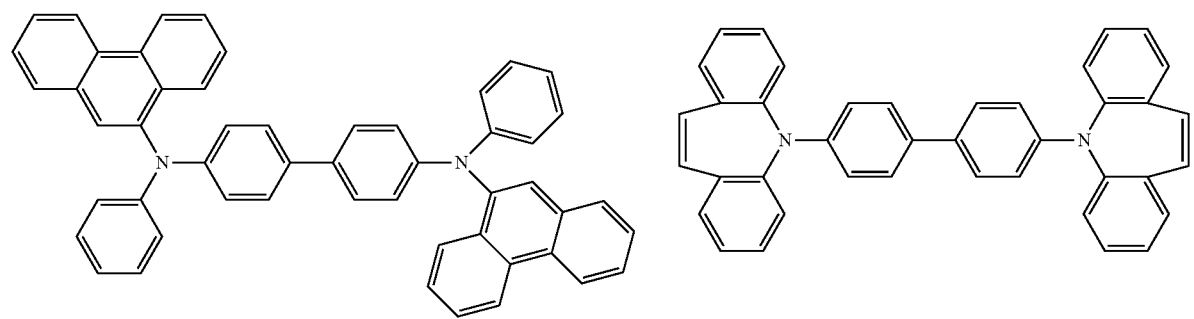
[Chemical Formula 68]
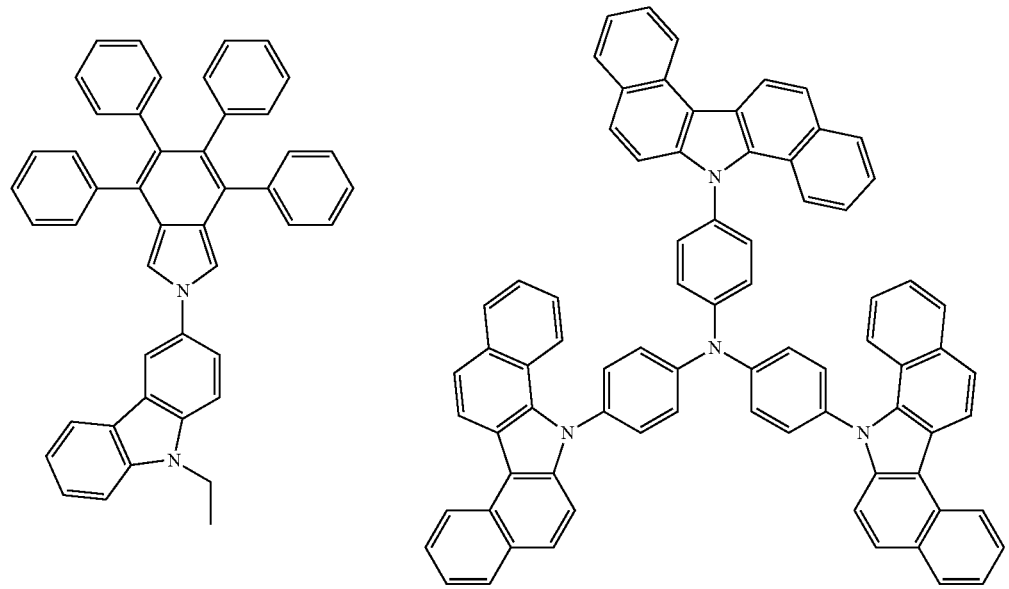

-continued
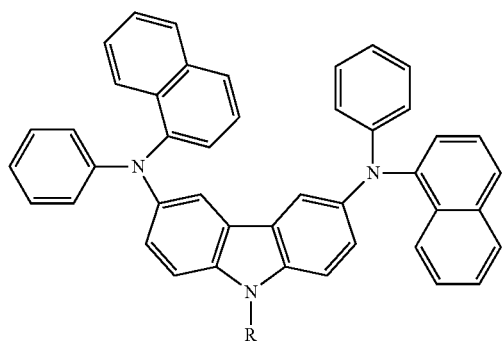
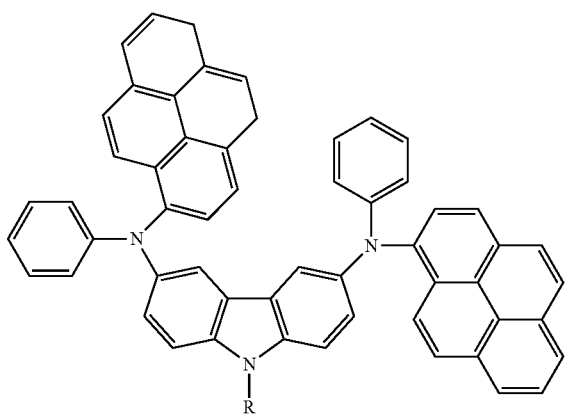
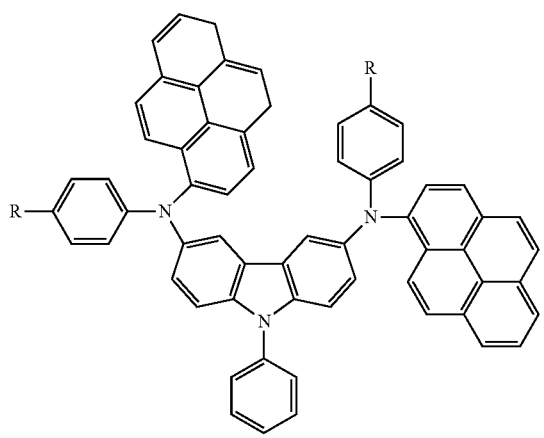
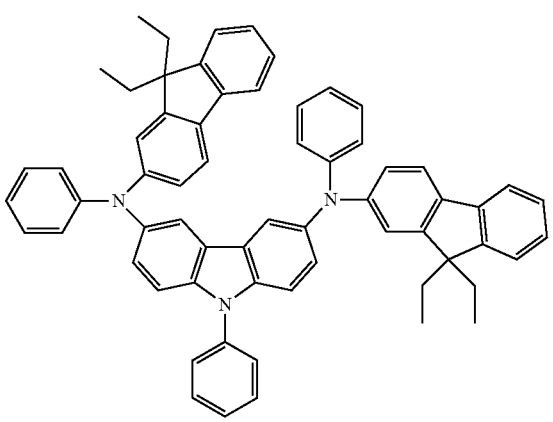
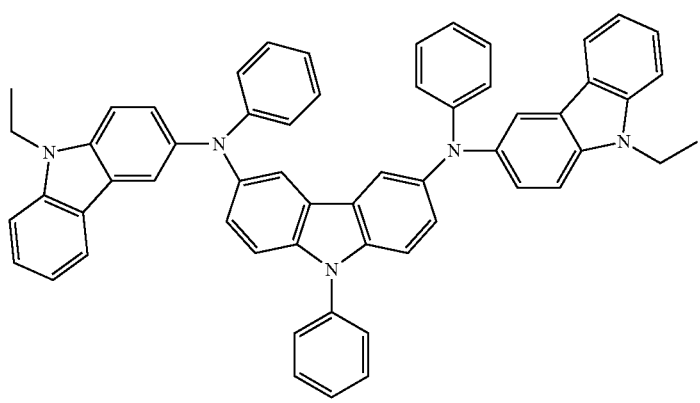
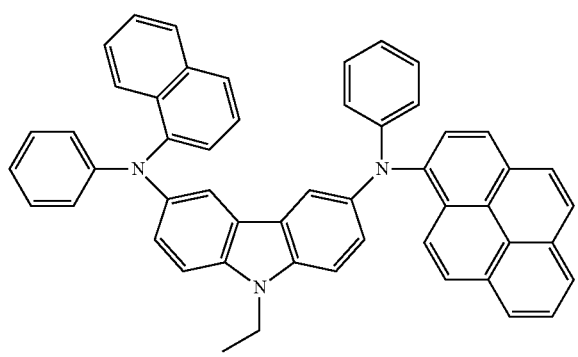

-continued
[Chemical Formula 69]
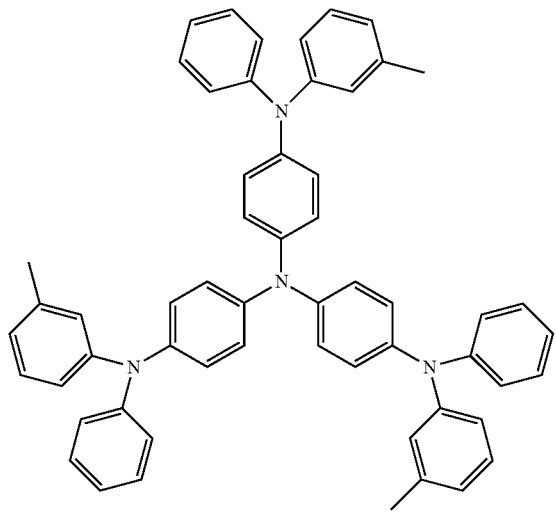
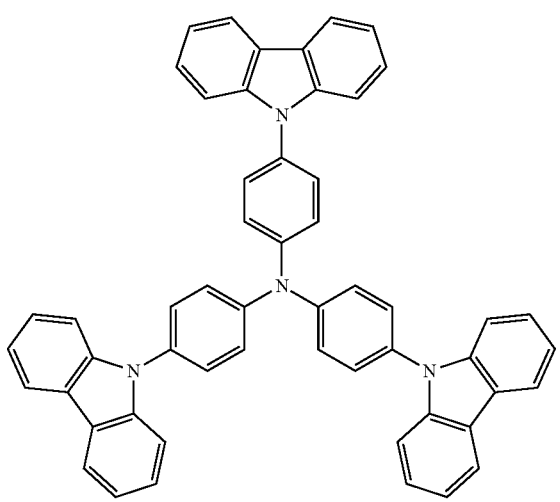
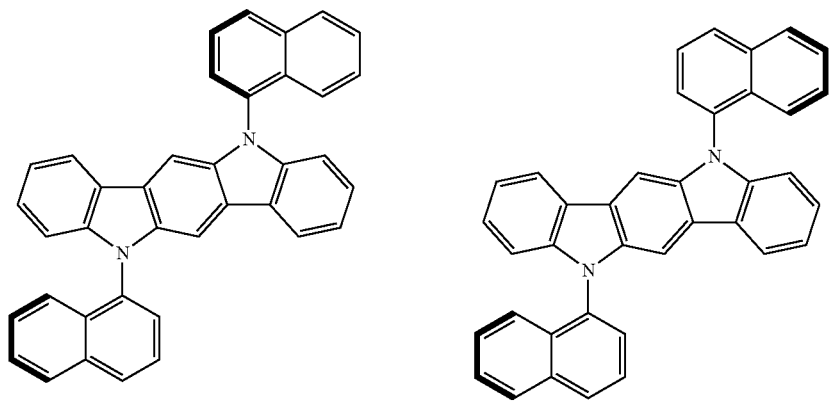
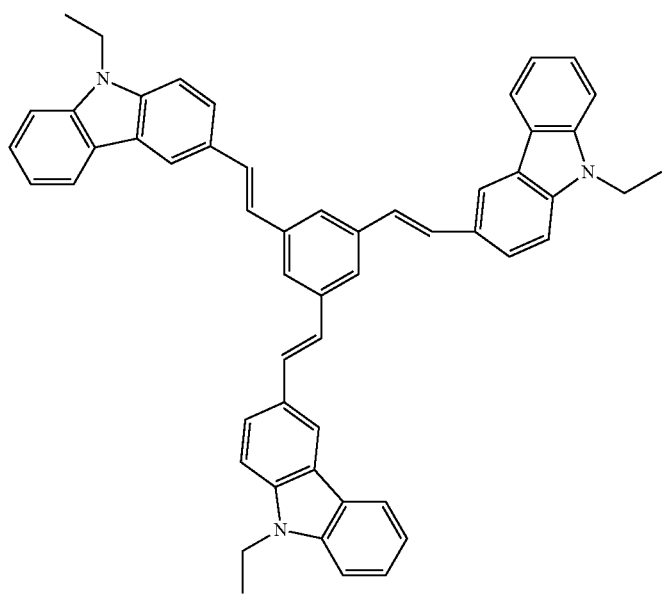

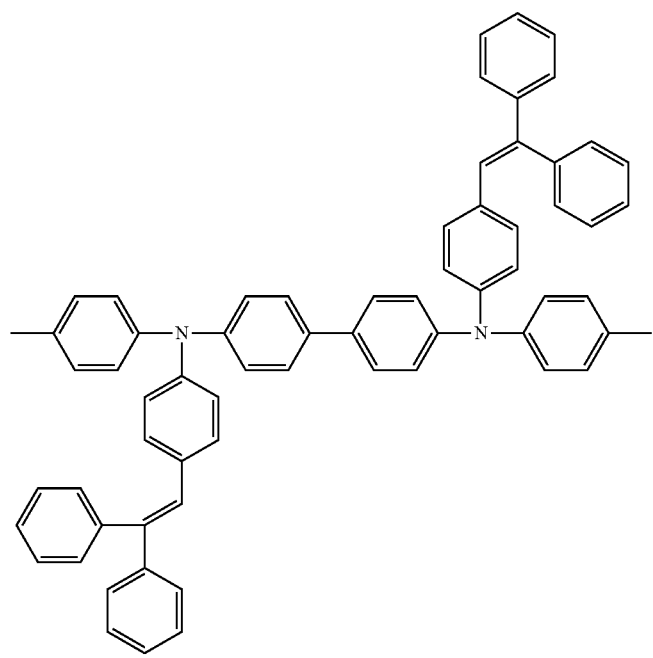
[Chemical Formula 70]
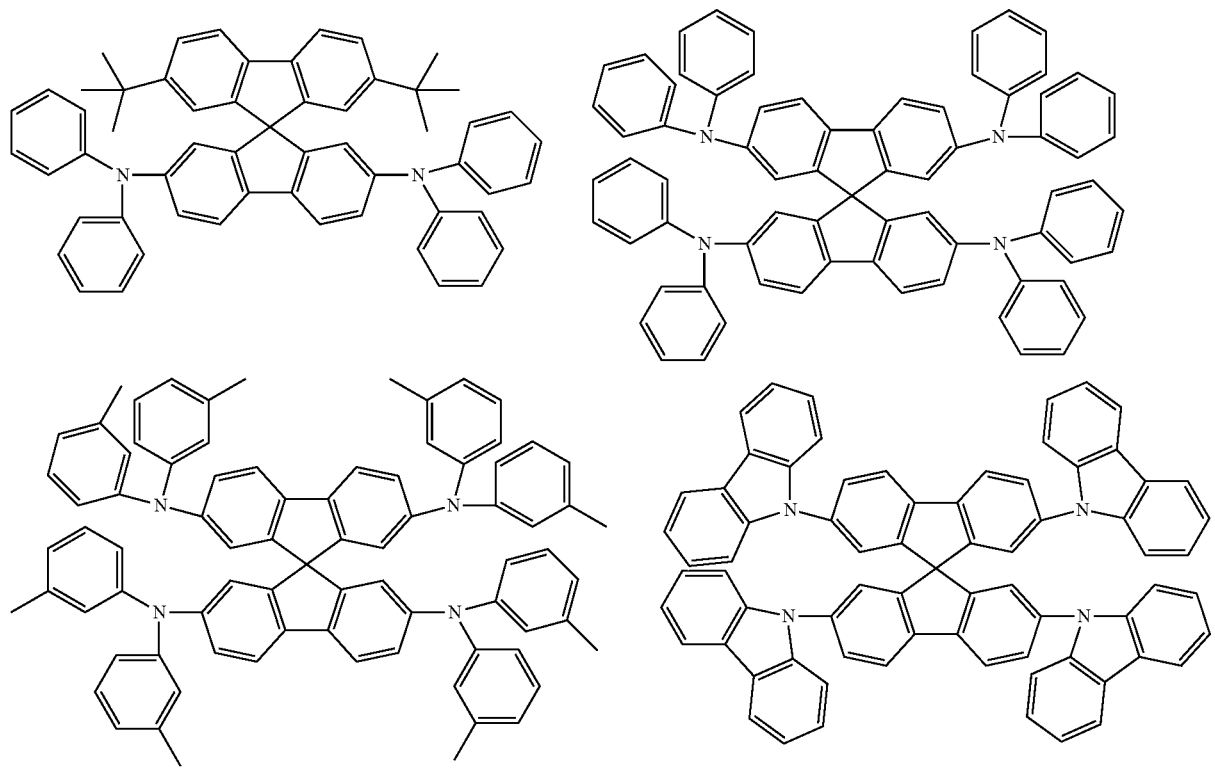
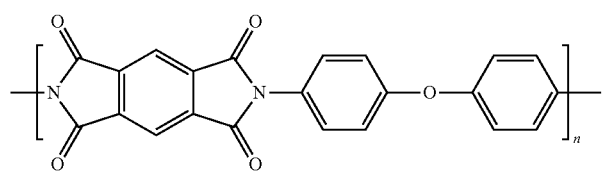

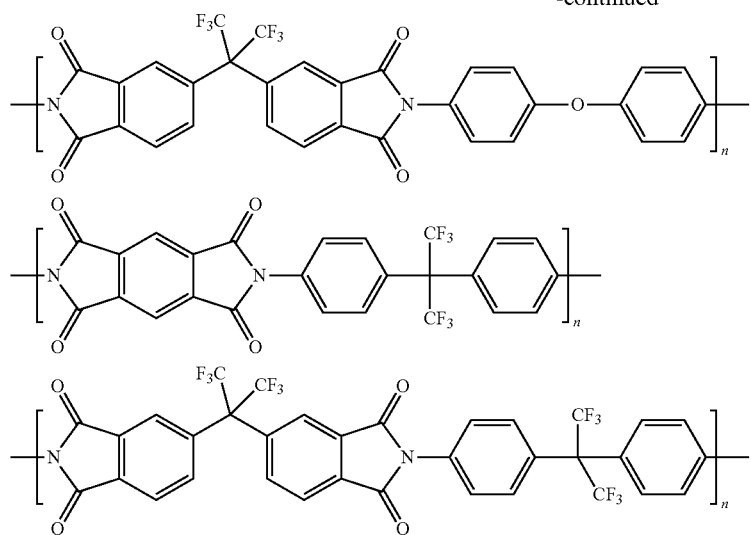
[Chemical Formula 71]
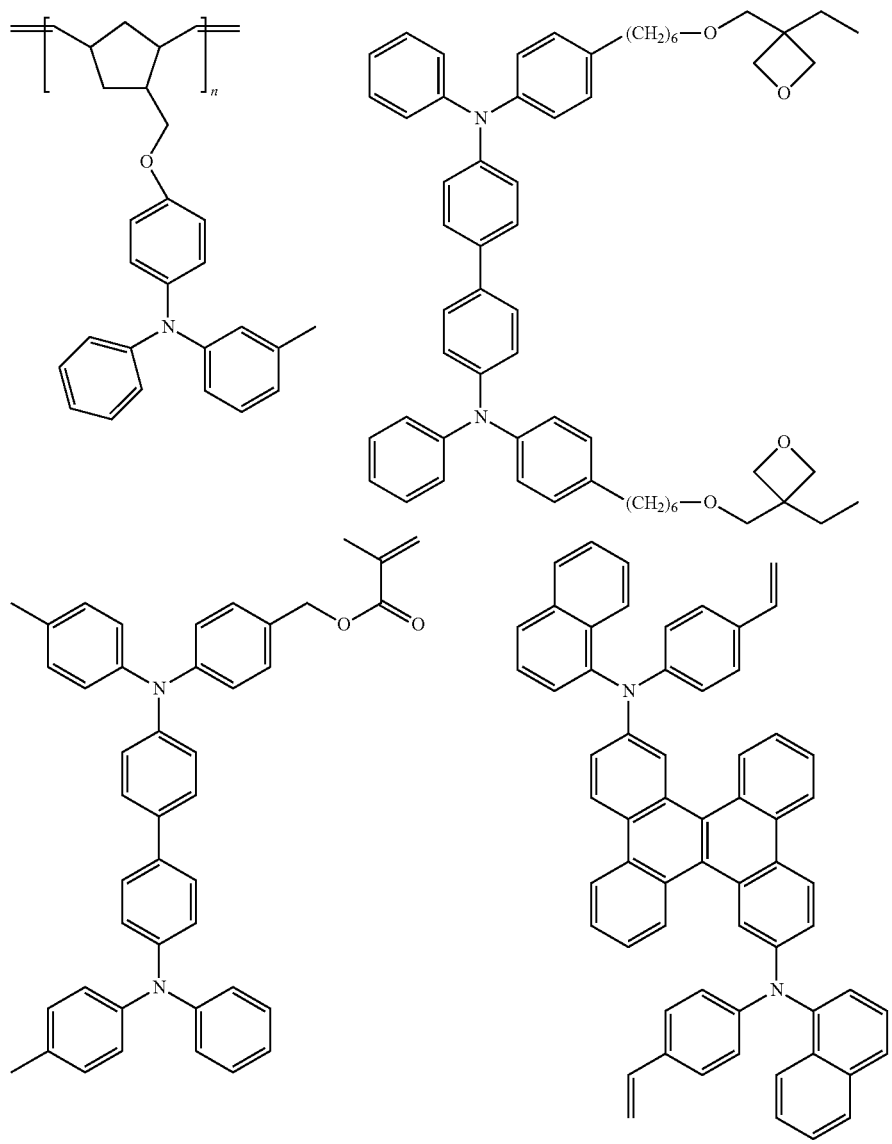

-continued
R = 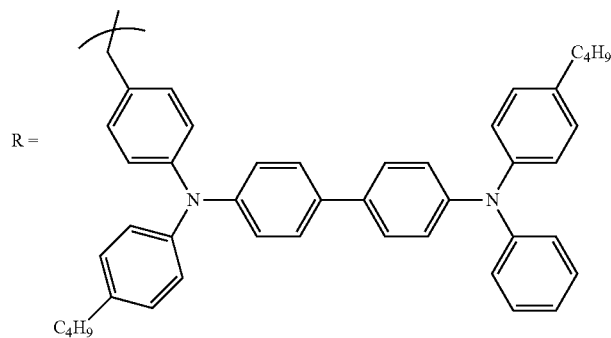
[Chemical Formula 72]
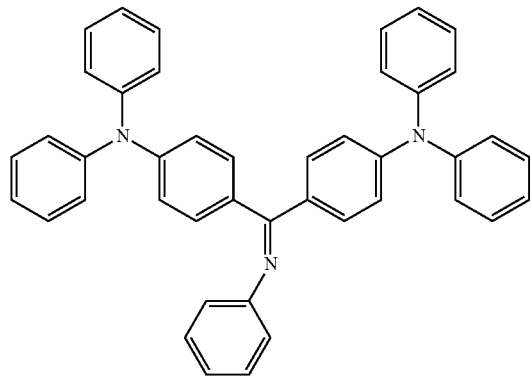
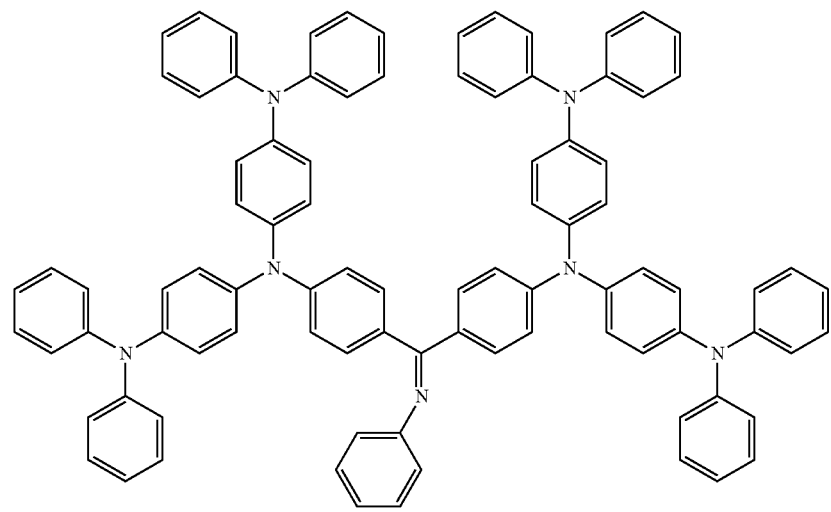

-continued
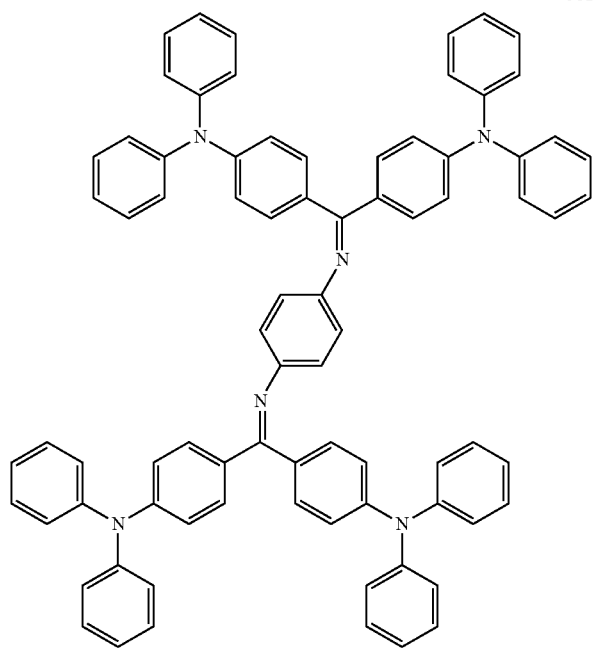
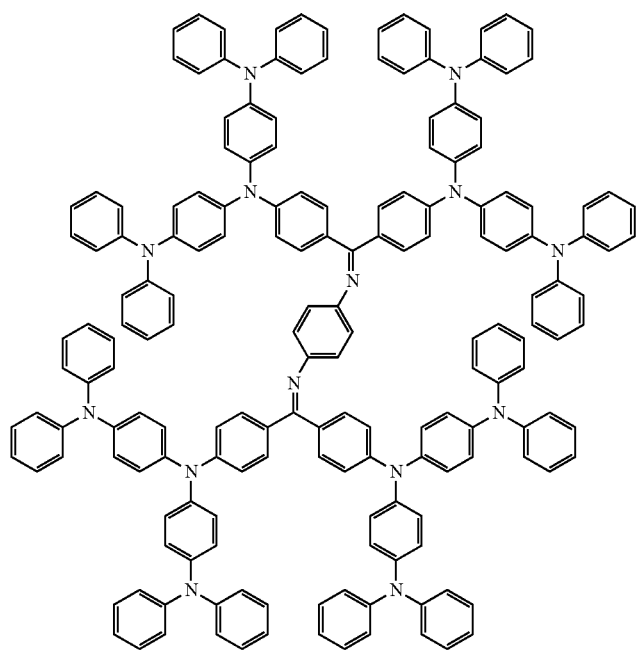

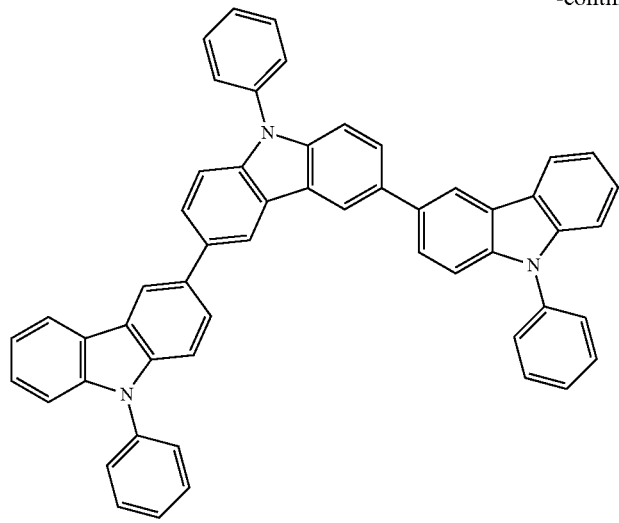
Preferred examples of a compound that may also be used as the material of the electron blocking layer are shown below.
[Chemical Formula 73]
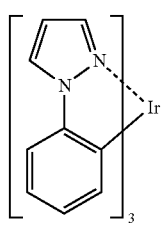
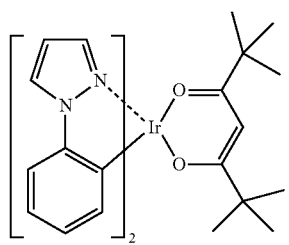
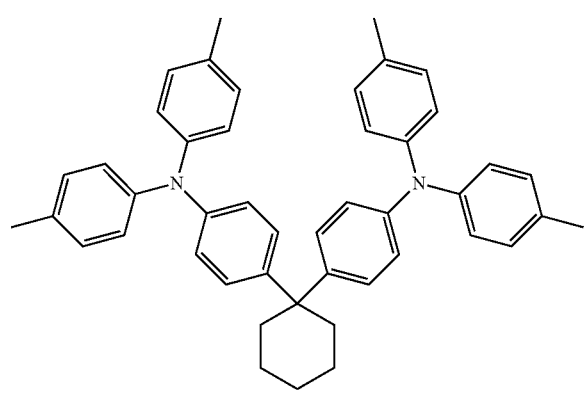
-continued
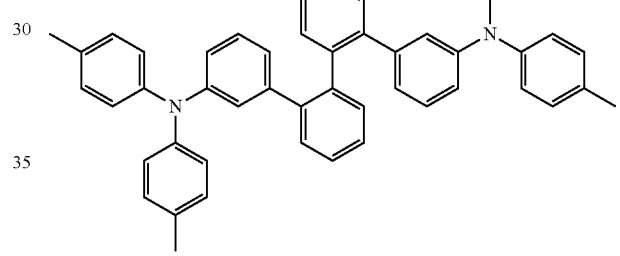
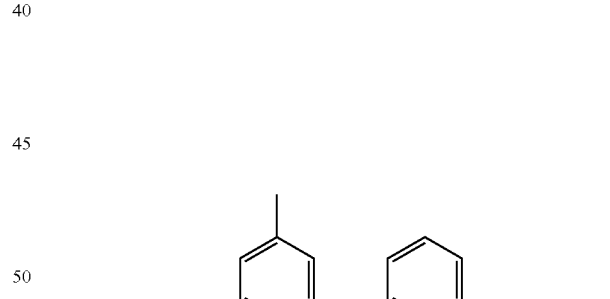
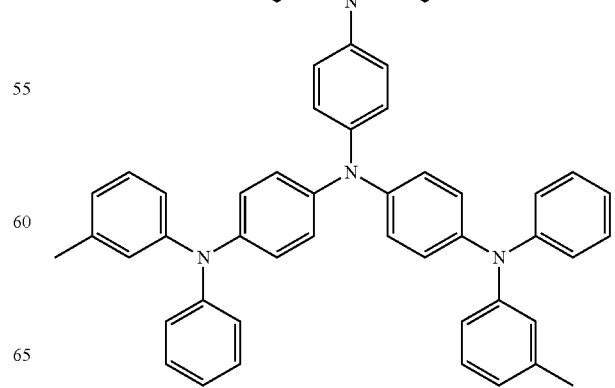

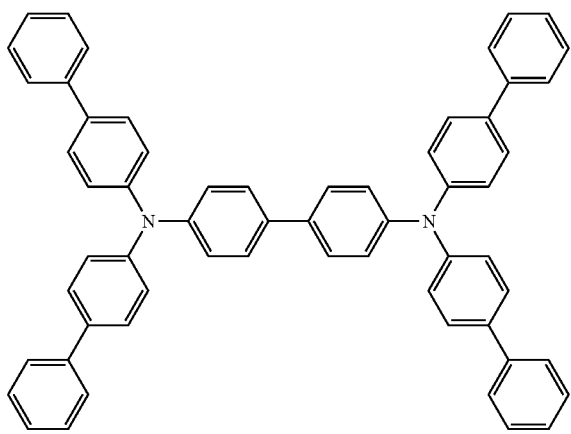 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
Preferred examples of a compound that may also be used as the material of the hole blocking layer are shown below.
[Chemical Formula 74]
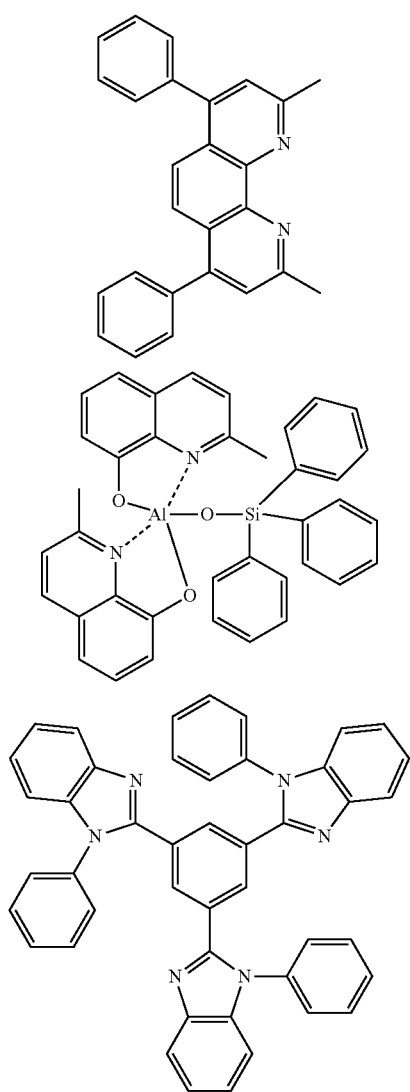
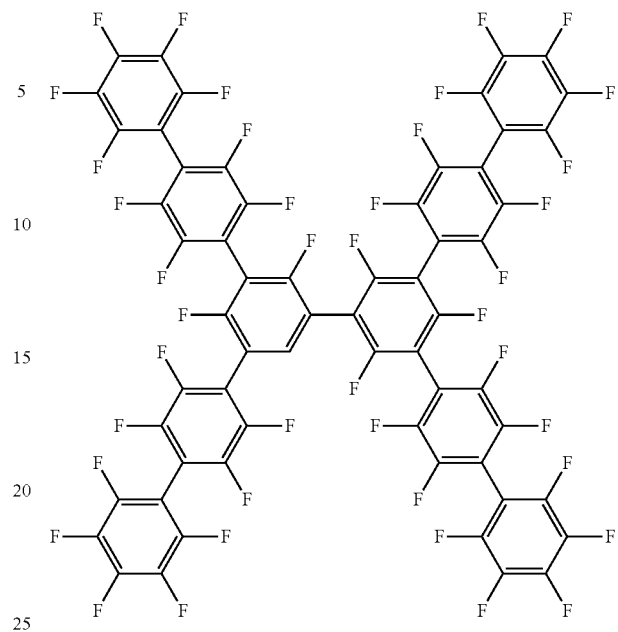
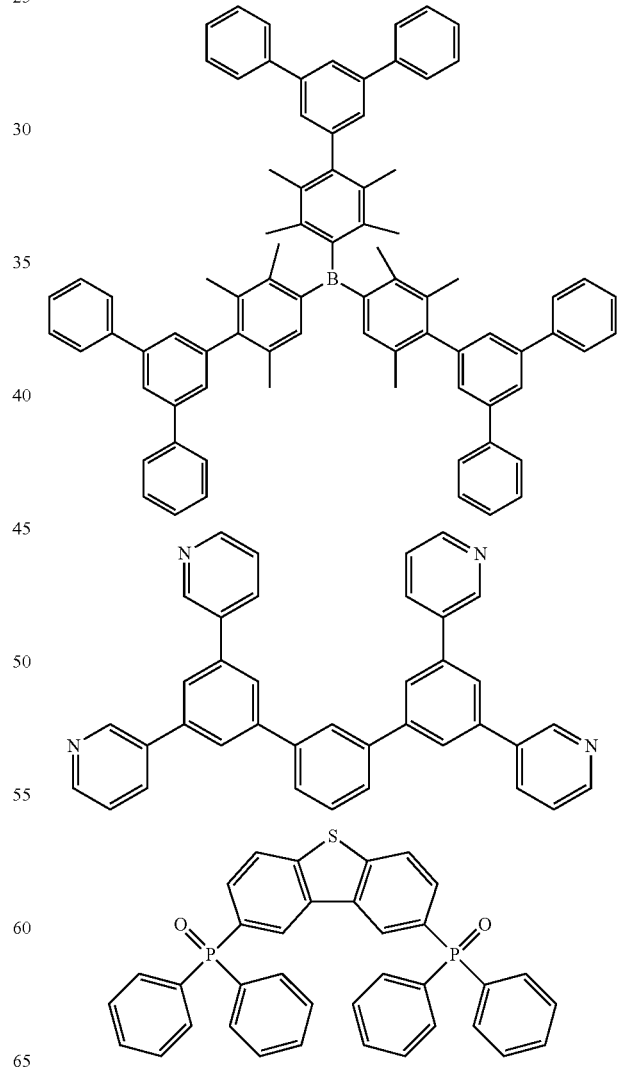

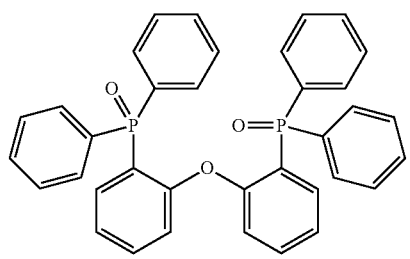
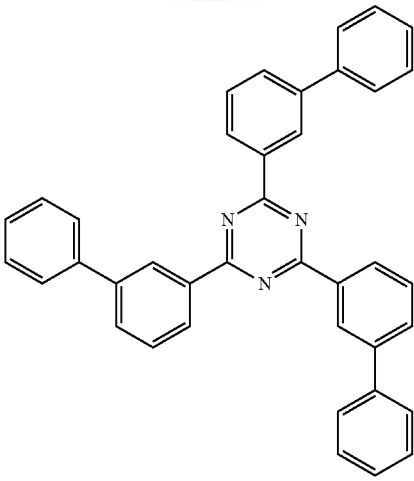
Preferred examples of a compound that may also be used as the material of the electron transport layer are shown below.
[Chemical Formula 75]
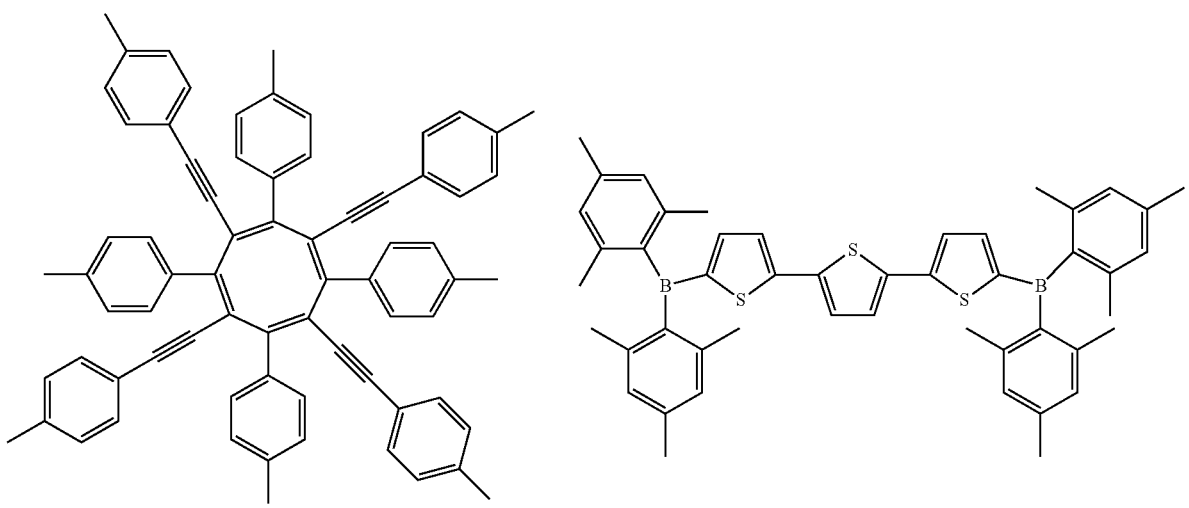
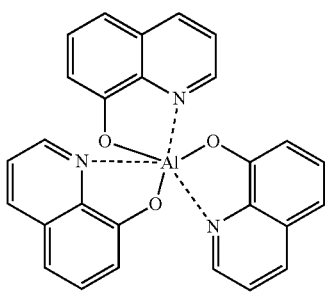
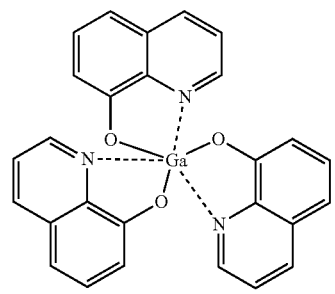
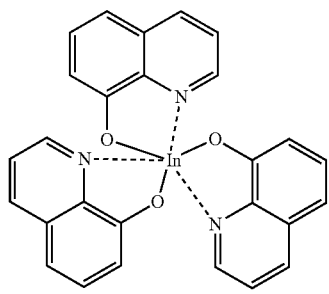

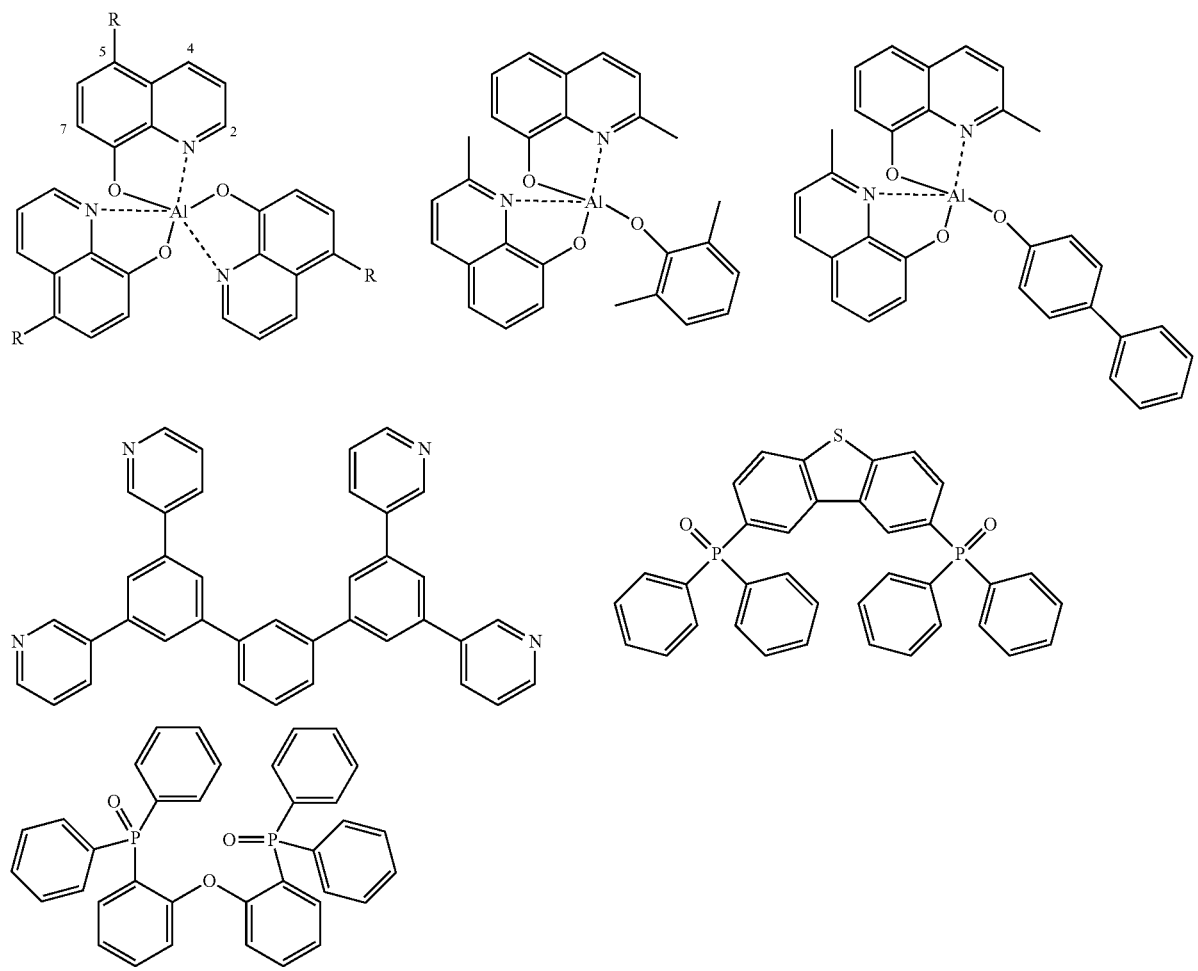
[Chemical Formula 76]
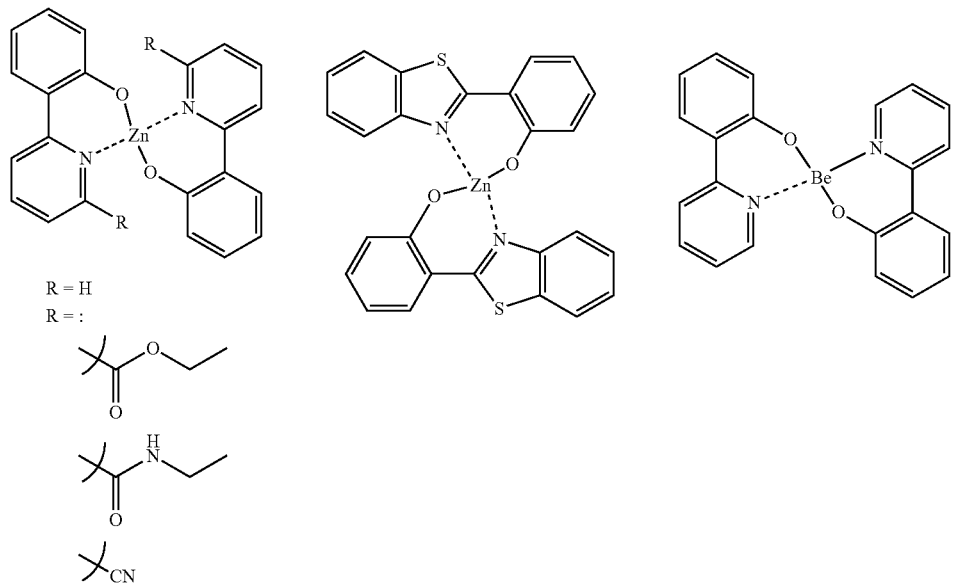

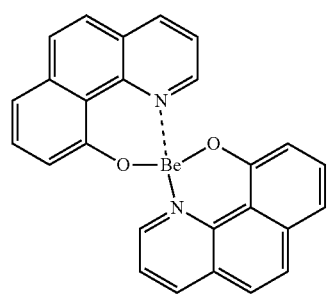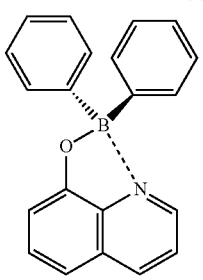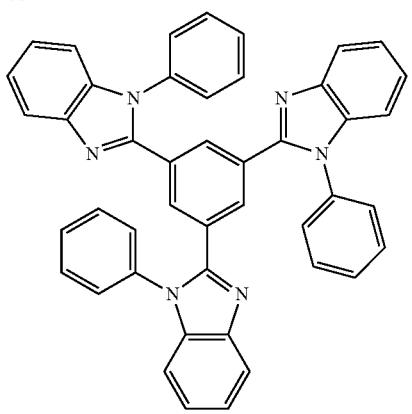
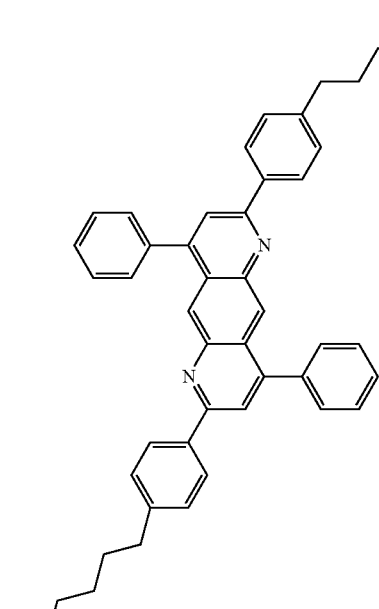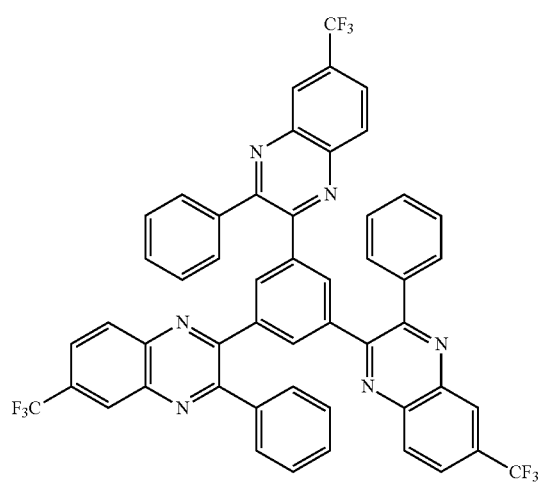
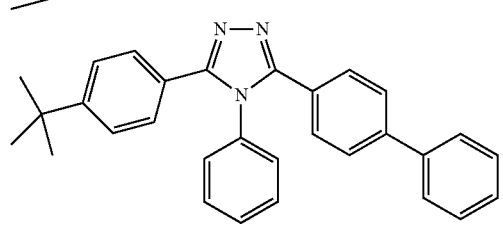
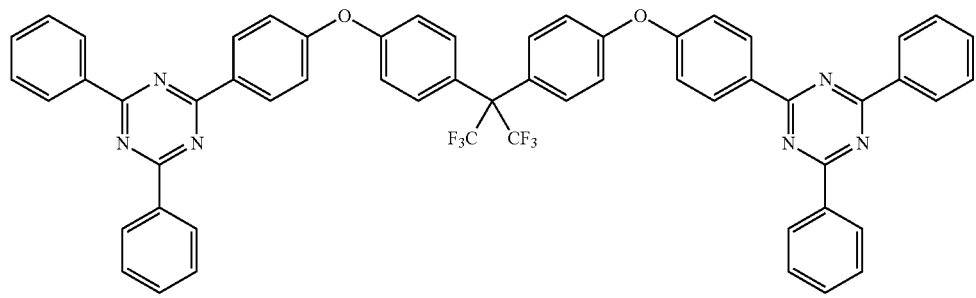
[Chemical Formula 77]
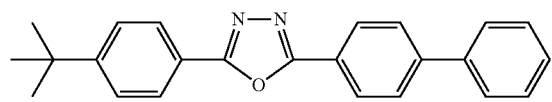

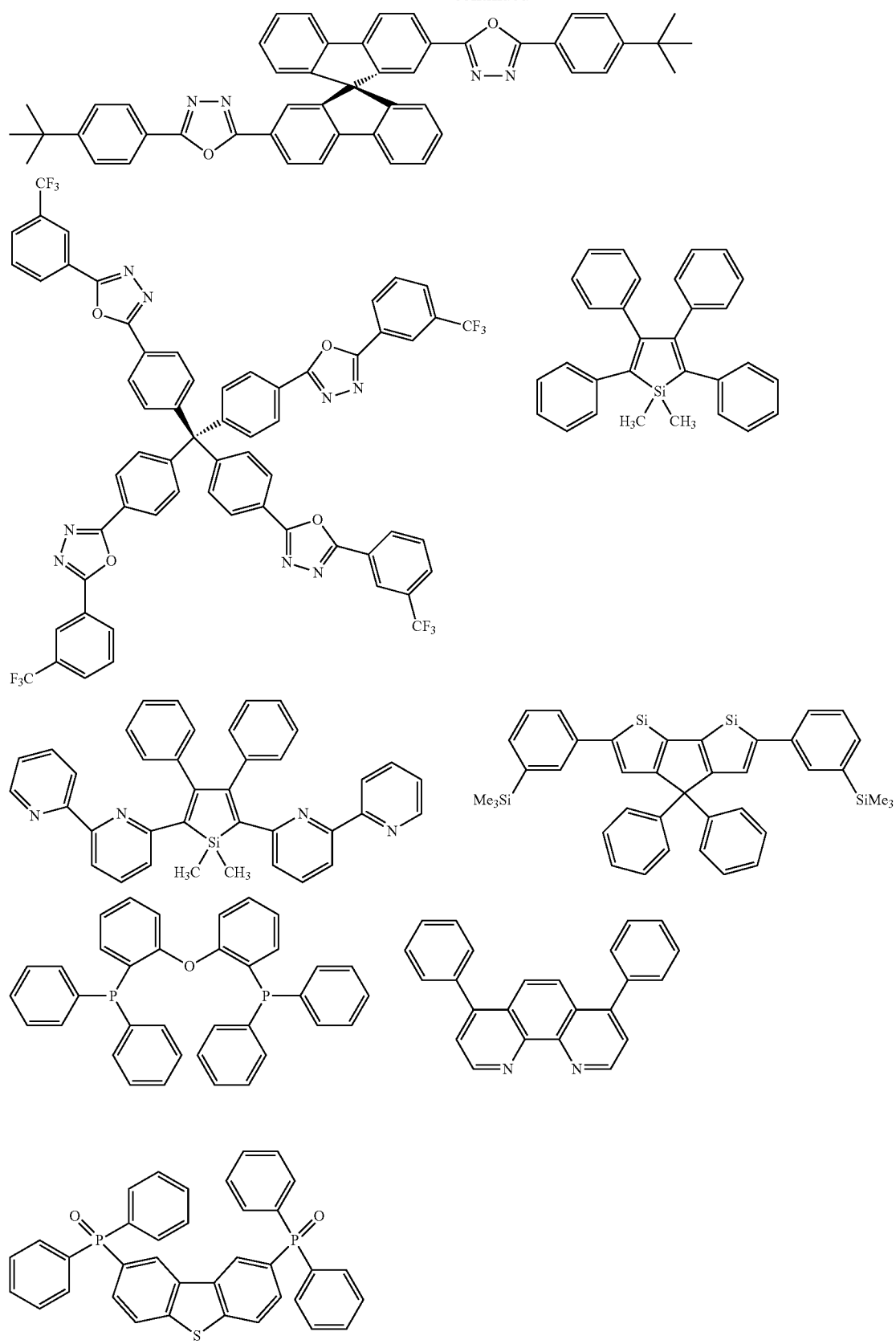

Preferred examples of a compound that may also be used as the material of the electron injection layer are shown below.

[Chemical Formula 78]

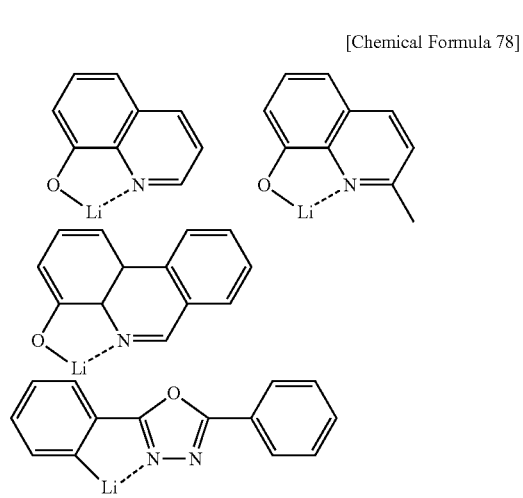

Preferred examples of a compound as a material that may be added are shown below. For example, the compound may be added as a stabilizing material.

[Chemical Formula 79]

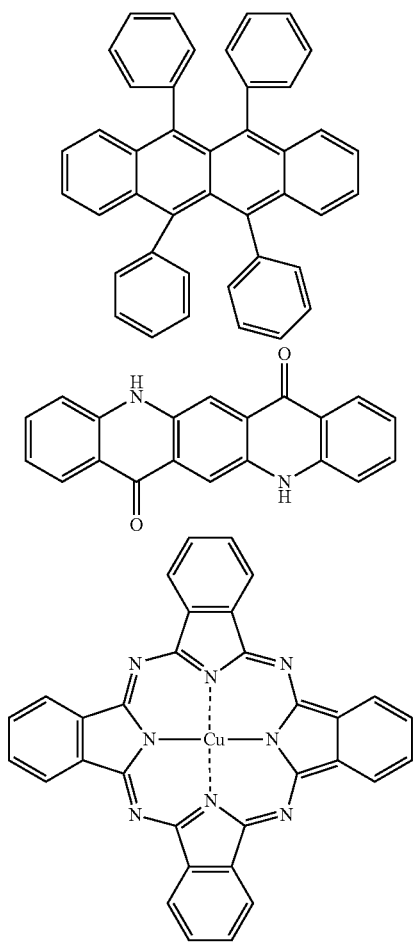

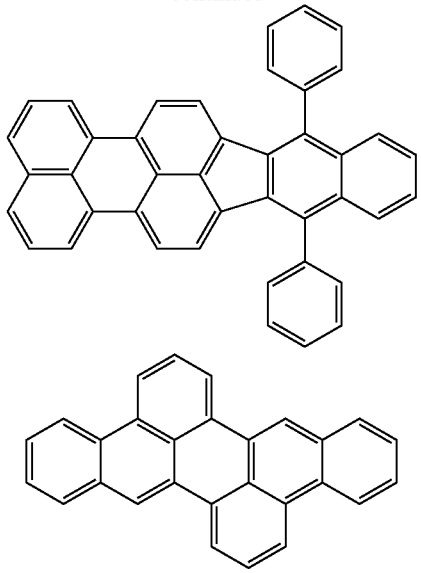

The following describes an embodiment of the present invention in more detail based on Examples. The present invention, however, is not restricted to the following Examples.

Example 1

Synthesis of 3,4-bis(carbazol-9-yl)benzonitrile (Compound 5)

To a reaction vessel having been substituted with nitrogen, N-methylpyrrolidone (100 mL), sodium hydride (60% suspension in oil, 2.1 g), carbazole (9.1 g), and 3,4-difluorobenzonitrile (3.0 g) were added and heated, and stirred at 120° C. for 18 hours. After allowing to cool to room temperature, water was added, and extraction was performed with toluene. The organic layer was concentrated, and purified by column chromatography, thereby providing a white solid matter of 3,4-bis(carbazol-9-yl)benzonitrile (Compound 5) (yield: 25%).

[Chemical Formula 80]

(Compound 5)

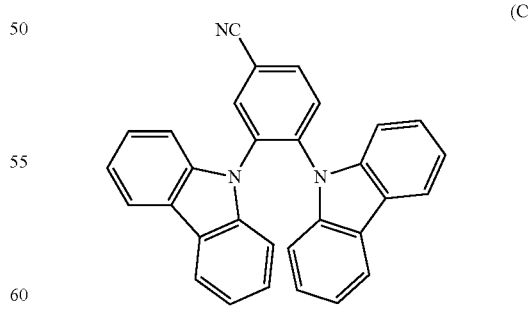

The structure of the obtained white solid was identified by NMR. The 1H-NMR measurement result is presented in FIG. 1.

$^1$H-NMR (CDCl$_3$) detected 19 hydrogen signals, as follows.

δ (ppm)=7.00-7.16 (12H), 7.74-7.85 (4H), 7.95 (1H), 7.98 (1H), 8.16 (1H).

Example 2

Synthesis of 3,4-bis(3,6-dimethylcarbazol-9-yl)benzonitrile (Compound 11)

To a reaction vessel having been substituted with nitrogen, N-methylpyrrolidone (100 mL), sodium hydride (60% suspension in oil, 2.1 g), 3,6-dimethylcarbazole (9.9 g), and 3,4-difluorobenzonitrile (3.0 g) were added and heated, and stirred at 120° C. for 24 hours. After allowing to cool to room temperature, water was added, and extraction was performed with toluene. The organic layer was concentrated, and purified by column chromatography, thereby providing a white solid matter of 3,4-bis(3,6-dimethylcarbazol-9-yl)benzonitrile (Compound 11) (yield: 53%).

[Chemical Formula 81]

(Compound 11)

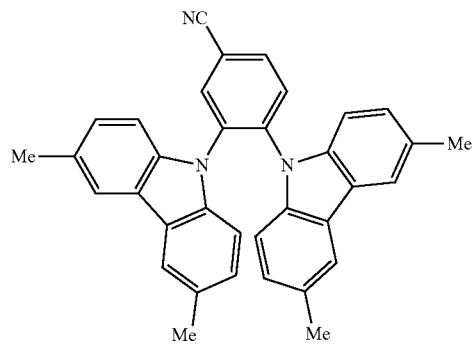

Figure 2:
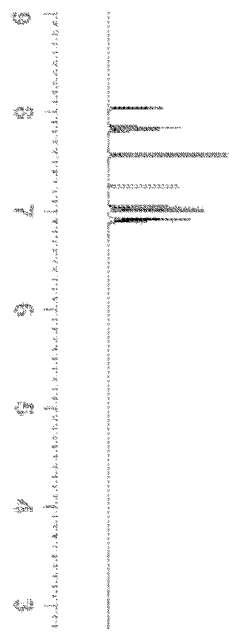
FIG. 2 is a $^1$H-NMR chart of the compound (Compound 11) of Example 2 of the present invention.

The structure of the obtained white solid was identified by NMR. The 1H-NMR measurement result is presented in FIG. 2.
$^1$H-NMR (CDCl$_3$) detected 27 hydrogen signals, as follows.
δ (ppm)=2.36 (12H), 6.91 (4H), 7.01 (2H), 7.03 (2H), 7.57 (4H), 7.81 (1H), 7.85 (1H), 8.06 (1H).

Example 3

Synthesis of 3,4,5-tris(carbazol-9-yl)benzonitrile (Compound 18)

To a reaction vessel having been substituted with nitrogen, N-methylpyrrolidone (50 mL), potassium carbonate (3.8 g), carbazole (4.8 g), and 3,4,5-trifluorobenzonitrile (1.0 g) were added and heated, and stirred at 120° C. for 30 hours. After allowing to cool to room temperature, water was added, and extraction was performed with toluene. The organic layer was concentrated, and purified by column chromatography, thereby providing a white solid matter of 3,4,5-tris(carbazol-9-yl)benzonitrile (Compound 18) (yield: 60%).

[Chemical Formula 82]

(Compound 18)

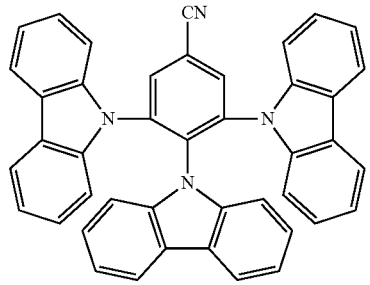

Figure 3:
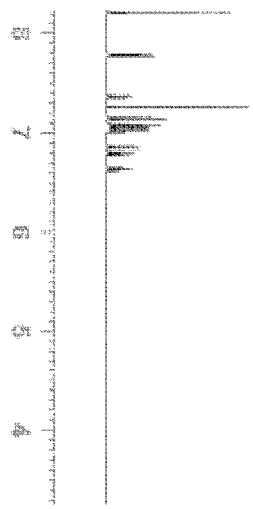
FIG. 3 is a $^1$H-NMR chart of the compound (Compound 18) of Example 3 of the present invention.

The structure of the obtained white solid was identified by NMR. The 1H-NMR measurement result is presented in FIG. 3.
$^1$H-NMR (CDCl$_3$) detected 26 hydrogen signals, as follows.
δ (ppm)=6.63 (2H), 6.79 (2H), 6.85 (2H), 6.98-7.12 (8H), 7.14 (4H), 7.36 (2H), 7.77 (4H), 8.22 (2H).

Example 4

A 100 nm-thick vapor-deposited film was fabricated on an ITO substrate using the compound of the compound of Example 1 (Compound 5). The work function was measured using an atmosphere photoelectron spectrometer (AC-3 produced by Riken Keiki Co., Ltd.).
Work function 6.10 eV Compound of Example 1

Thus, the benzonitrile derivatives of the general formula (1) have work functions greater than the work function 5.4 eV of common hole transport materials such as NPD and TPD, and have high hole blocking capability.

Example 5

A toluene solution of 10$^{-5}$ mol/L of the compound of Example 1 (Compound 5) was prepared. The toluene solution was irradiated with ultraviolet light at 300 K while blowing nitrogen therein, and thereby fluorescence having a peak wavelength of 406 nm was observed.
The toluene solution was measured for the time-resolved spectrum before and after the nitrogen blowing, with Compact Fluorescence Lifetime Spectrometer, Quantaurus-tau, produced by Hamamatsu Photonics K.K., and thereby fluorescence having an emission lifetime of 0.01 μs and delayed fluorescence having an emission lifetime of 0.23 μs were observed.
The toluene solution was measured for the photoluminescence (hereinafter abbreviated as PL) quantum efficiency before and after the nitrogen blowing, with Absolute PL Quantum Yield Spectrometer, Quantaurus-QY, produced by Hamamatsu Photonics K.K., at 300 K, and the PL quantum efficiency was 25% before the nitrogen blowing and 58% after the nitrogen blowing.

Example 6

The characteristics evaluation was performed in the same manner as in Example 5 except that a toluene solution of 10$^{-5}$ mol/L of the compound of Example 3 (Compound 18)

was prepared instead of the compound of Example 1 (Compound 5). As a result, fluorescence having a peak wavelength of 438 nm was observed, and fluorescence having an emission lifetime of 0.02 μs and delayed fluorescence having an emission lifetime of 1.2 μs were observed.

The PL quantum efficiency was 22% before the nitrogen blowing and 36% after the nitrogen blowing.

Example 7

Figure 4:
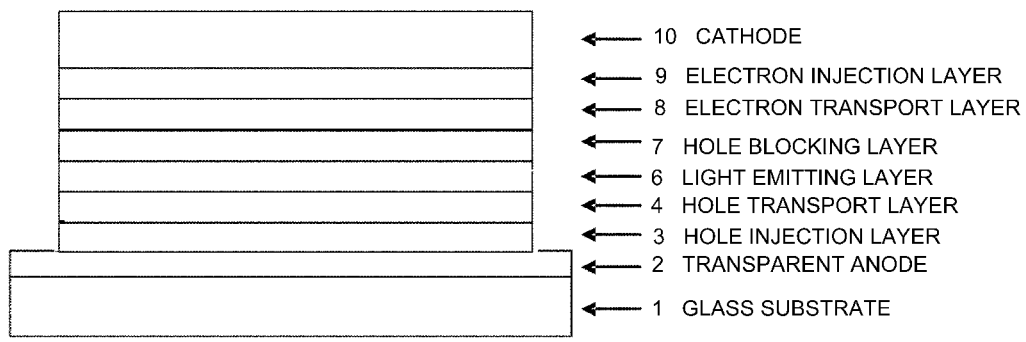
FIG. 4 is a diagram illustrating the configuration of the EL devices of Example 7 and Comparative Example 1.

The organic EL device, as shown in FIG. 4, was fabricated by vapor-depositing a hole injection layer 3, a hole transport layer 4, a light emitting layer 6, a hole blocking layer 7, an electron transport layer 8, an electron injection layer 9, and a cathode (aluminum electrode) 10 in this order on a glass substrate 1 on which an ITO electrode was formed as a transparent anode 2 beforehand.

Specifically, the glass substrate 1 having ITO (a thickness of 100 nm) formed thereon was washed with an organic solvent, and subjected to a UV ozone treatment to wash the surface. The glass substrate with the ITO electrode was then installed in a vacuum vapor deposition apparatus, and the pressure was reduced to 0.001 Pa or less.

Subsequently, the compound HATCN of the following structural formula was formed to a thickness of 10 nm as the hole injection layer 3 to cover the transparent anode 2. On the hole injection layer 3, the compound Tris-PCz of the following structural formula was formed to a thickness of 35 nm as the hole transport layer 4. On the hole transport layer 4, the compound 4CzIPN of the following structural formula and the compound of Example 1 (Compound 5) were subjected to dual vapor deposition at a vapor deposition rate providing a vapor deposition rate ratio of (4CzIPN)/(Compound of Example 1 (Compound 5)) of 10/90 to a thickness of 30 nm as the light emitting layer 6. On the light emitting layer 6, the compound T2T of the following structural formula was formed to a thickness of 10 nm as the hole blocking layer 7. On the hole blocking layer 7, the compound BPy-TP2 of the following structural formula was formed to a thickness of 40 nm as the electron transport layer 8. On the electron transport layer 8, lithium fluoride was formed to a thickness of 0.8 nm as the electron injection layer 9. Finally, aluminum was vapor-deposited to a thickness of 100 nm to form the cathode 10. The characteristics of the organic EL device were measured in the atmosphere at ordinary temperature.

[Chemical Formula 83]

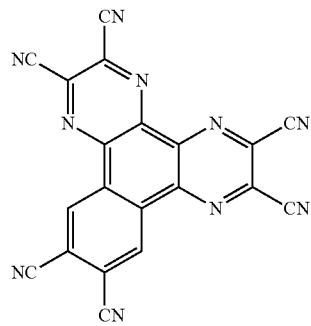

(HATCN)

[Chemical Formula 84]

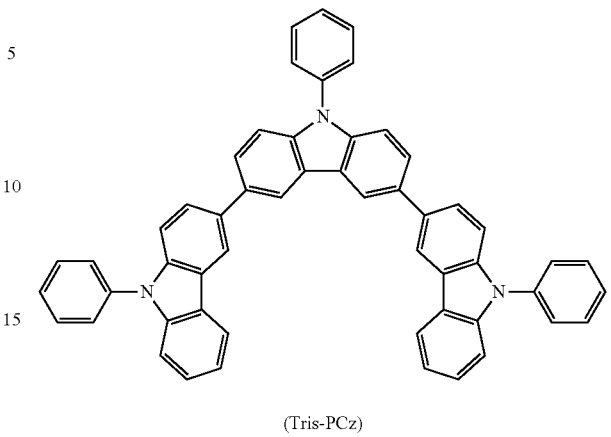

(Tris-PCz)

[Chemical Formula 85]

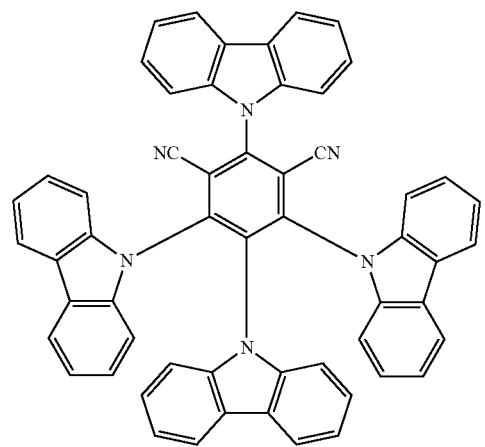

(4CzIPN)

[Chemical Formula 86]

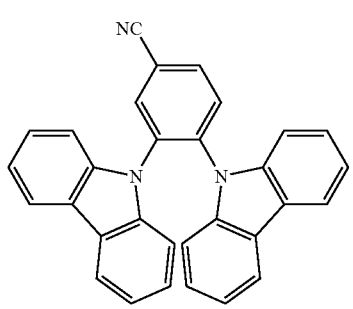

(Compound 5)

-continued

[Chemical Formula 87]

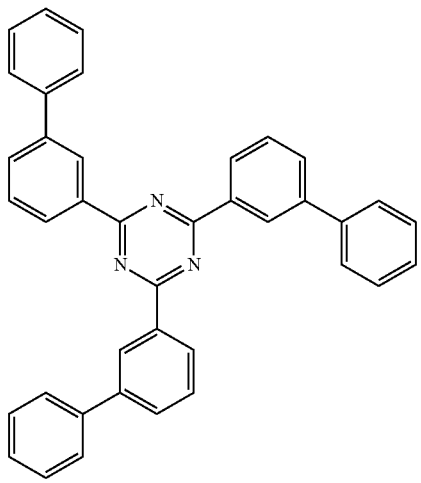

(T2T)

[Chemical Formula 88]

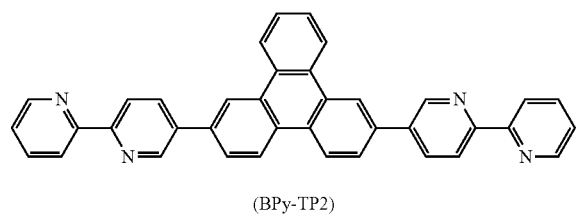

(BPy-TP2)

A direct current voltage having a current density of 10 mA/cm² was applied to the organic EL device produced with the compound of Example 1 (Compound 5), and the luminous efficiency was 41.0 cd/A.

The organic EL device produced with the compound of Example 1 (Compound 5) was measured for the extent of the roll-off phenomenon. The extent of the roll-off phenomenon was measured as the ratio of the external quantum efficiency on application of an electric current having a current density of 10 mA/cm² with respect to the external quantum efficiency on application of an electric current having a current density of 1 mA/cm² as 100 (relative quantum efficiency, %). As a result, the relative quantum efficiency was 108%.

Comparative Example 1

For comparison, an organic EL device was produced under the same condition as in Example 7 except that the compound mCBP of the following structural formula was used as the material of the light emitting layer 6 instead of the compound of Example 1 (Compound 5), and the compound 4CzIPN and mCBP were subjected to dual vapor deposition at a vapor deposition rate providing a vapor deposition rate ratio of (4CzIPN)/(mCBP) of 10/90 to a thickness of 30 nm. The characteristics of the organic EL device were measured in the atmosphere at ordinary temperature. A direct current voltage having a current density of 10 mA/cm² was applied to the organic EL device thus produced, and the luminous efficiency was 30.6 cd/A. The relative quantum efficiency was 42%.

[Chemical Formula 89]

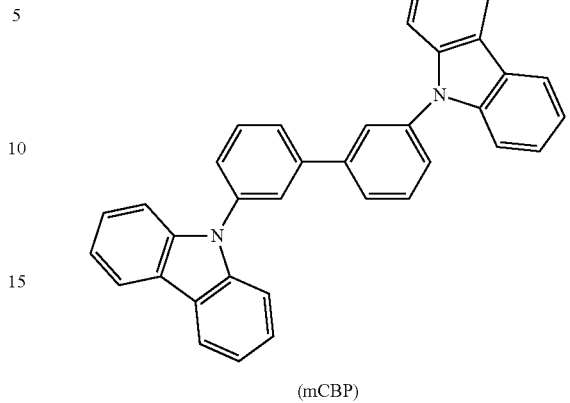

(mCBP)

As described above, the luminous efficiency on application of an electric current having a current density of 10 mA/cm² was 41.0 cd/A for the organic EL device of Example 7 using the compound of Example 1 (Compound 5), which was largely enhanced as compared to 30.6 cd/A for the organic EL device of Comparative Example 1 using mCBP. As for the relative quantum efficiency, the organic EL device of Example 7 was 108%, from which no roll-off phenomenon was observed, but the organic EL device of Comparative Example 1 was 42% indicating decrease by half in quantum efficiency, from which a large roll-off phenomenon was observed.

Example 8

Figure 5:
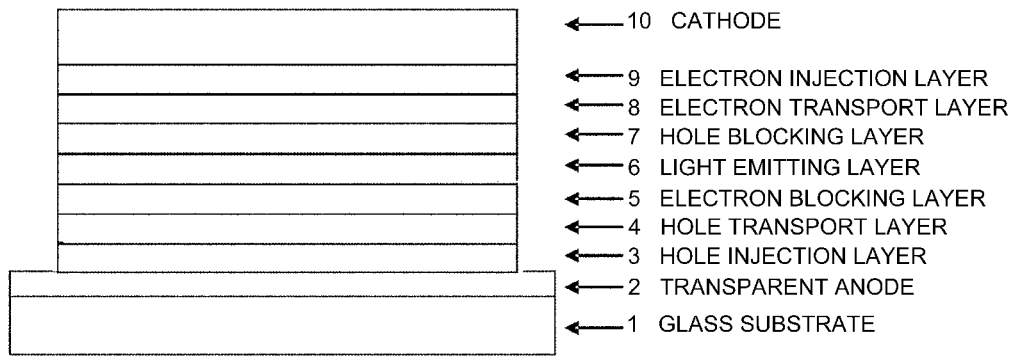
FIG. 5 is a diagram illustrating the configuration of the EL devices of Example 8.

The organic EL device, as shown in FIG. 5, was fabricated by vapor-depositing a hole injection layer 3, a hole transport layer 4, an electron blocking layer 5, a light emitting layer 6, a hole blocking layer 7, an electron transport layer 8, an electron injection layer 9, and a cathode (aluminum electrode) 10 in this order on a glass substrate 1 on which an ITO electrode was formed as a transparent anode 2 beforehand.

Specifically, the glass substrate 1 having ITO (a thickness of 100 nm) formed thereon was washed with an organic solvent, and subjected to a UV ozone treatment to wash the surface. The glass substrate with the ITO electrode was then installed in a vacuum vapor deposition apparatus, and the pressure was reduced to 0.001 Pa or less.

Subsequently, the compound HATCN of the aforementioned structural formula was formed to a thickness of 10 nm as the hole injection layer 3 to cover the transparent anode 2. On the hole injection layer 3, the compound Tris-PCz of the aforementioned structural formula was formed to a thickness of 35 nm as the hole transport layer 4. On the hole transport layer 4, the compound mCP of the following structural formula was formed to a thickness of 10 nm as the electron blocking layer 5. On the electron blocking layer 5, the compound 3CzTRZ of the following structural formula and the compound of Example 1 (Compound 5) were subjected to dual vapor deposition at a vapor deposition rate providing a vapor deposition rate ratio of (3CzTRZ)/(Compound of Example 1 (Compound 5)) of 10/90 to a thickness of 30 nm as the light emitting layer 6. On the light emitting layer 6, the compound of Example 1 (Compound 5) was formed to a thickness of 10 nm as the hole blocking layer 7. On the hole blocking layer 7, the compound BPy-TP2 of the aforementioned structural formula was formed to a thickness of 40 nm as the electron transport layer 8. On the electron transport layer 8, lithium fluoride was formed to a thickness of 0.8 nm as the electron injection layer 9. Finally, aluminum was vapor-deposited to a thickness of 100 nm to form the cathode 10. The characteristics of the organic EL device were measured in the atmosphere at ordinary temperature.

[Chemical Formula 90]

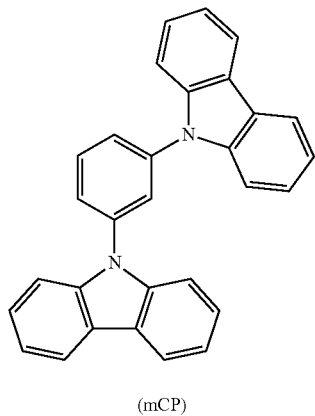

(mCP)

[Chemical Formula 91]

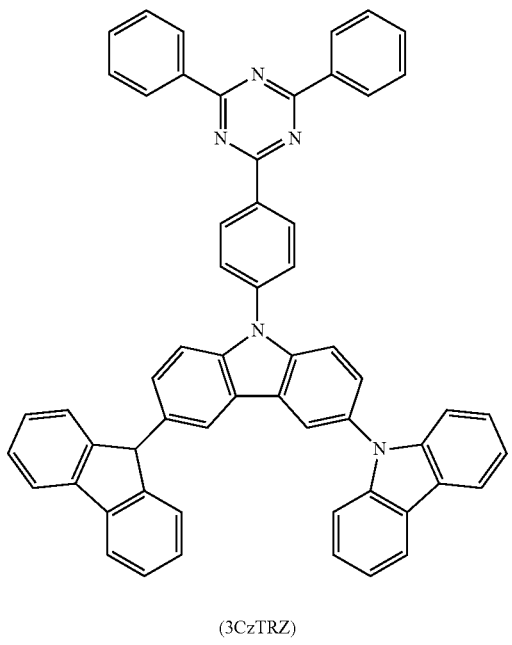

(3CzTRZ)

The organic EL device produced with the compound of Example 1 (Compound 5) had a relative quantum efficiency of 87%.

As described above, the organic EL device of Example 8 had a relative quantum efficiency of 87%, from which it was found that the roll-off phenomenon was largely suppressed as compared to the organic EL device of Comparative Example 1 having a relative quantum efficiency of 42%.

Example 9

Figure 6:
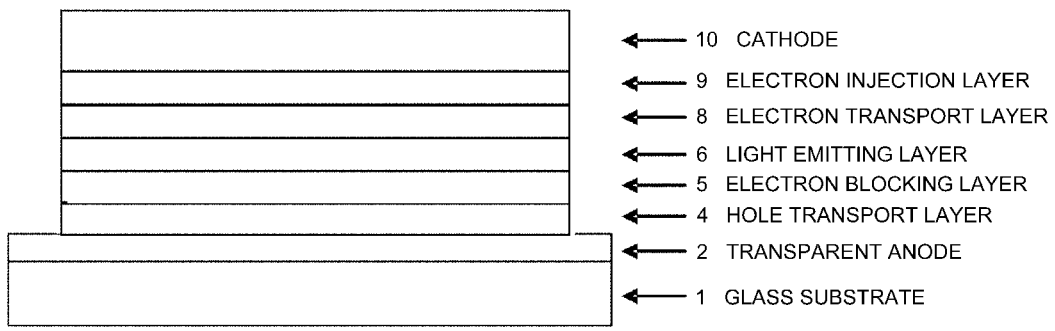
FIG. 6 is a diagram illustrating the configuration of the EL devices of Example 9.

The organic EL device, as shown in FIG. 6, was fabricated by vapor-depositing a hole transport layer 4, an electron blocking layer 5, a light emitting layer 6, an electron transport layer 8, an electron injection layer 9, and a cathode (aluminum electrode) 10 in this order on a glass substrate 1 on which an ITO electrode was formed as a transparent anode 2 beforehand.

Specifically, the glass substrate 1 having ITO (a thickness of 100 nm) formed thereon was washed with an organic solvent, and subjected to a UV ozone treatment to wash the surface. The glass substrate with the ITO electrode was then installed in a vacuum vapor deposition apparatus, and the pressure was reduced to 0.001 Pa or less.

Subsequently, the compound NPD of the following structural formula was formed to a thickness of 35 nm as the hole transport layer 4 to cover the transparent anode 2. On the hole transport layer 4, the compound mCP of the aforementioned structural formula was formed to a thickness of 10 nm as the electron blocking layer 5. On the electron blocking layer 5, the compound of Example 3 (Compound 18) and the compound PPT of the following structural formula were subjected to dual vapor deposition at a vapor deposition rate providing a vapor deposition rate ratio of (Compound of Example 3 (Compound 18))/(PPT) of 5/95 to a thickness of 15 nm as the light emitting layer 6. On the light emitting layer 6, the compound PPT of the following structural formula was formed to a thickness of 40 nm as the electron transport layer 8. On the electron transport layer 8, lithium fluoride was formed to a thickness of 0.8 nm as the electron injection layer 9. Finally, aluminum was vapor-deposited to a thickness of 100 nm to form the cathode 10. The characteristics of the organic EL device were measured in the atmosphere at ordinary temperature.

[Chemical Formula 92]

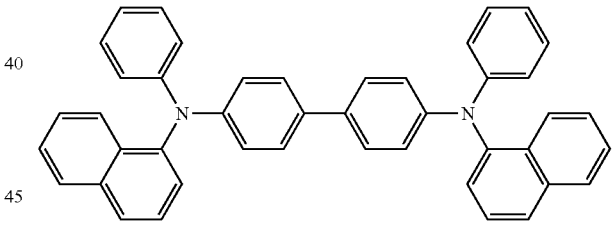

(NPD)

[Chemical Formula 93]

(Compound 18)

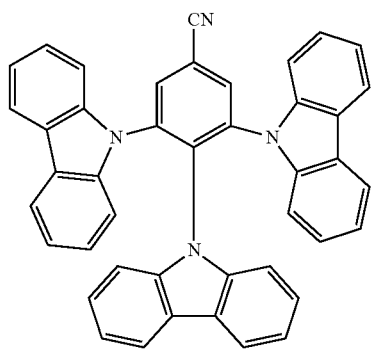

[Chemical Formula 94]

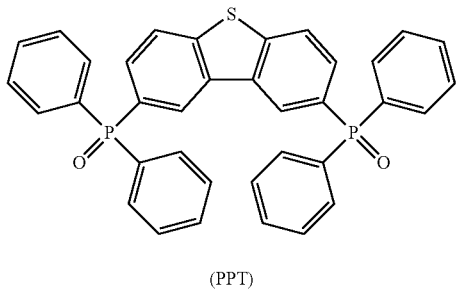

(PPT)

The organic EL device produced with the compound of Example 3 (Compound 18) had a maximum value of the external quantum efficiency of 13.0% on application of a direct current voltage.

As described above, it was found that the compound having a benzonitrile structure of the present invention can emit delayed fluorescence and has a large external quantum efficiency.

INDUSTRIAL APPLICABILITY

The benzonitrile derivative represented by the general formula (1) can emit delayed fluorescence and has good thin film stability, and thus the benzonitrile derivative is excellent as a material of a light emitting layer, particularly a dopant material of a light emitting layer. The benzonitrile derivative has a favorable energy level and a favorable capability of confinement of the triplet energy, and thus the benzonitrile derivative is excellent as a material of a light emitting layer, particularly a host material of a light emitting layer, and as a material of a hole blocking layer. The use of the compound as a material of an organic EL device can drastically improve the luminance and the luminous efficiency of the ordinary organic EL device. Furthermore, the decrease of the luminous efficiency (external quantum efficiency) on increase of the current density can be suppressed, and the roll-off phenomenon of the luminous efficiency (external quantum efficiency) can be effectively suppressed.

REFERENCE SIGNS LIST

1 Glass substrate
2 Transparent anode
3 Hole injection layer
4 Hole transport layer
5 Electron blocking layer
6 Light emitting layer
7 Hole blocking layer
8 Electron transport layer
9 Electron injection layer
10 Cathode

The invention claimed is:

1. An organic electroluminescent device comprising a pair of electrodes and one layer or plural layers including at least a light emitting layer intervening between the electrodes, the light emitting layer containing as a constitutional material thereof a light-emitting material comprising a benzonitrile derivative of the following general formula (1),

[Chemical Formula 1]

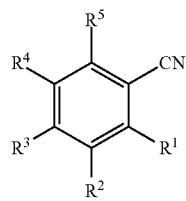

(1)

wherein $R^1$ to $R^5$ may be the same or different, and each represent a hydrogen atom, a deuterium atom, a fluorine atom, a chlorine atom, nitro, linear or branched alkyl of 1 to 6 carbon atoms, which may have a substituent, cycloalkyl of 5 to 10 carbon atoms, which may have a substituent, linear or branched alkenyl of 2 to 6 carbon atoms, which may have a substituent, linear or branched alkyloxy of 1 to 6 carbon atoms, which may have a substituent, cycloalkyloxy of 5 to 10 carbon atoms, which may have a substituent, a substituted or unsubstituted aromatic hydrocarbon group, a substituted or unsubstituted aromatic heterocyclic group, a substituted or unsubstituted condensed polycyclic aromatic group, a substituted or unsubstituted aryloxy group, or a disubstituted amino group substituted with a group selected from an aromatic hydrocarbon group, an aromatic heterocyclic group, and a condensed polycyclic aromatic group, and may bind to each other via a single bond, substituted or unsubstituted methylene, an oxygen atom, or a sulfur atom, to form a ring, provided that at least one of $R^1$ to $R^5$ represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group, wherein the light-emitting material is used as a dopant material of the light emitting layer, and wherein the organic electroluminescent device emits delayed fluorescence.

2. The organic electroluminescent device according to claim 1, wherein at least one of $R^1$ to $R^5$ of the general formula (1) is a group selected from a substituted or unsubstituted aromatic heterocyclic group, and a disubstituted amino group substituted with a group selected from an aromatic hydrocarbon group, an aromatic heterocyclic group, and a condensed polycyclic aromatic group.

3. The organic electroluminescent device according to claim 2, wherein at least one of $R^1$ to $R^5$ of the general formula (1) is a substituted or unsubstituted aromatic heterocyclic group.

4. The organic electroluminescent device according to claim 3, wherein at least one of $R^1$ to $R^5$ of the general formula (1) is a substituted or unsubstituted nitrogen-containing aromatic heterocyclic group.

5. The organic electroluminescent device according to claim 4, wherein at least one of $R^1$ to $R^5$ of the general formula (1) is a monovalent group selected from substituted or unsubstituted phenoxazinyl, substituted or unsubstituted phenothiazinyl, substituted or unsubstituted acridinyl, substituted or unsubstituted phenazinyl, substituted or unsubstituted carbazolyl, and substituted or unsubstituted carbolinyl.

6. The organic electroluminescent device according to claim 1, wherein $R^2$ of the general formula (1) is a group selected from a substituted or unsubstituted aromatic hydrocarbon group, a substituted or unsubstituted aromatic heterocyclic group, a substituted or unsubstituted condensed polycyclic aromatic group, and a disubstituted amino group substituted with a group selected from an aromatic hydrocarbon group, an aromatic heterocyclic group, and a condensed polycyclic aromatic group.

7. The organic electroluminescent device according to claim 1, wherein $R^3$ of the general formula (1) is a group selected from a substituted or unsubstituted aromatic hydrocarbon group, a substituted or unsubstituted aromatic heterocyclic group, a substituted or unsubstituted condensed polycyclic aromatic group, and a disubstituted amino group substituted with a group selected from an aromatic hydrocarbon group, an aromatic heterocyclic group, and a condensed polycyclic aromatic group.

8. An organic electroluminescent device comprising a pair of electrodes and one layer or plural layers including at least a light emitting layer intervening between the electrodes, the light emitting layer containing as a constitutional material thereof a light-emitting material comprising a benzonitrile derivative of the following general formula (1),

[Chemical Formula 1]

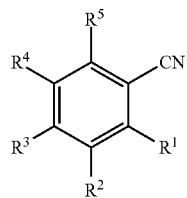

(1)

wherein $R^1$ to $R^5$ may be the same or different, and each represent a hydrogen atom, a deuterium atom, a fluorine atom, a chlorine atom, nitro, linear or branched alkyl of 1 to 6 carbon atoms, which may have a substituent, cycloalkyl of 5 to 10 carbon atoms, which may have a substituent, linear or branched alkenyl of 2 to 6 carbon atoms, which may have a substituent, linear or branched alkyloxy of 1 to 6 carbon atoms, which may have a substituent, cycloalkyloxy of 5 to 10 carbon atoms, which may have a substituent, a substituted or unsubstituted aromatic hydrocarbon group, a substituted or unsubstituted aromatic heterocyclic group, a substituted or unsubstituted condensed polycyclic aromatic group, a substituted or unsubstituted aryloxy group, or a disubstituted amino group substituted with a group selected from an aromatic hydrocarbon group, an aromatic heterocyclic group, and a condensed polycyclic aromatic group, and may bind to each other via a single bond, substituted or unsubstituted methylene, an oxygen atom, or a sulfur atom, to form a ring, provided that at least one of $R^1$ to $R^5$ represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group,
wherein the light-emitting material is used as a dopant material of the light emitting layer, and
wherein $R^2$ and $R^3$ of the general formula (1) is a group selected from a substituted or unsubstituted aromatic hydrocarbon group, a substituted or unsubstituted aromatic heterocyclic group, a substituted or unsubstituted condensed polycyclic aromatic group, and a disubstituted amino group substituted with a group selected from an aromatic hydrocarbon group, an aromatic heterocyclic group, and a condensed polycyclic aromatic group.

9. An organic electroluminescent device comprising a pair of electrodes and one layer or plural layers including at least a light emitting layer intervening between the electrodes, the light emitting layer containing as a constitutional material thereof a light-emitting material comprising a benzonitrile derivative of the following general formula (1),

[Chemical Formula 1]

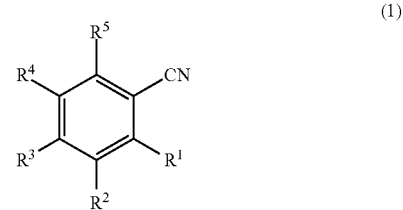

(1)

wherein $R^1$ to $R^5$ may be the same or different, and each represent a hydrogen atom, a deuterium atom, a fluorine atom, a chlorine atom, nitro, linear or branched alkyl of 1 to 6 carbon atoms, which may have a substituent, cycloalkyl of 5 to 10 carbon atoms, which may have a substituent, linear or branched alkenyl of 2 to 6 carbon atoms, which may have a substituent, linear or branched alkyloxy of 1 to 6 carbon atoms, which may have a substituent, cycloalkyloxy of 5 to 10 carbon atoms, which may have a substituent, a substituted or unsubstituted aromatic hydrocarbon group, a substituted or unsubstituted aromatic heterocyclic group, a substituted or unsubstituted condensed polycyclic aromatic group, a substituted or unsubstituted aryloxy group, or a disubstituted amino group substituted with a group selected from an aromatic hydrocarbon group, an aromatic heterocyclic group, and a condensed polycyclic aromatic group, and may bind to each other via a single bond, substituted or unsubstituted methylene, an oxygen atom, or a sulfur atom, to form a ring, provided that at least one of $R^1$ to $R^5$ represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group,
wherein the light-emitting material is used as a dopant material of the light emitting layer, and
wherein $R^2$, $R^3$ and $R^4$ of the general formula (1) is a group selected from a substituted or unsubstituted aromatic hydrocarbon group, a substituted or unsubstituted aromatic heterocyclic group, a substituted or unsubstituted condensed polycyclic aromatic group, and a disubstituted amino group substituted with a group selected from an aromatic hydrocarbon group, an aromatic heterocyclic group, and a condensed polycyclic aromatic group.

10. The organic electroluminescent device according to claim 8, wherein the at least one of $R^1$ to $R^5$ of the general formula (1) is a group selected from a substituted or unsubstituted aromatic heterocyclic group, and a disubstituted amino group substituted with a group selected from an aromatic hydrocarbon group, an aromatic heterocyclic group, and a condensed polycyclic aromatic group.

11. The organic electroluminescent device according to claim 8, wherein $R^2$ of the general formula (1) is a group selected from a substituted or unsubstituted aromatic hydrocarbon group, a substituted or unsubstituted aromatic heterocyclic group, a substituted or unsubstituted condensed polycyclic aromatic group, and a disubstituted amino group substituted with a group selected from an aromatic hydrocarbon group, an aromatic heterocyclic group, and a condensed polycyclic aromatic group.

12. The organic electroluminescent device according to claim 8, wherein $R^3$ of the general formula (1) is a group selected from a substituted or unsubstituted aromatic hydrocarbon group, a substituted or unsubstituted aromatic heterocyclic group, a substituted or unsubstituted condensed polycyclic aromatic group, and a disubstituted amino group substituted with a group selected from an aromatic hydrocarbon group, an aromatic heterocyclic group, and a condensed polycyclic aromatic group.

13. The organic electroluminescent device according to claim 8, wherein the light-emitting material emits delayed fluorescence.

14. The organic electroluminescent device according to claim 9, wherein the at least one of $R^1$ to $R^5$ of the general formula (1) is a group selected from a substituted or unsubstituted aromatic heterocyclic group, and a disubstituted amino group substituted with a group selected from an aromatic hydrocarbon group, an aromatic heterocyclic group, and a condensed polycyclic aromatic group.

15. The organic electroluminescent device according to claim 9, wherein $R^2$ of the general formula (1) is a group selected from a substituted or unsubstituted aromatic hydrocarbon group, a substituted or unsubstituted aromatic heterocyclic group, a substituted or unsubstituted condensed polycyclic aromatic group, and a disubstituted amino group substituted with a group selected from an aromatic hydrocarbon group, an aromatic heterocyclic group, and a condensed polycyclic aromatic group.

16. The organic electroluminescent device according to claim 9, wherein $R^3$ of the general formula (1) is a group selected from a substituted or unsubstituted aromatic hydrocarbon group, a substituted or unsubstituted aromatic heterocyclic group, a substituted or unsubstituted condensed polycyclic aromatic group, and a disubstituted amino group substituted with a group selected from an aromatic hydrocarbon group, an aromatic heterocyclic group, and a condensed polycyclic aromatic group.

17. The organic electroluminescent device according to claim 9, wherein the light-emitting material emits delayed fluorescence.

* * * * *